US012806325B2

(12) United States Patent
Kusters et al.

(10) Patent No.: US 12,806,325 B2

(45) Date of Patent: Nov. 24, 2026

(54) SYSTEMS AND METHODS FOR SETTING A CONTINUOUS-FLOW CENTRIFUGE ROTATION RATE

(71) Applicant: Fenwal, Inc., Lake Zurich, IL (US)

(72) Inventors: Benjamin E. Kusters, Pleasant Prairie, WI (US); Richard I. Brown, Northbrook, IL (US)

(73) Assignee: Fenwal, Inc., Lake Zurich, IL (US)

( * ) Notice: Subject to any disclaimer, the term of this patent is extended or adjusted under 35 U.S.C. 154(b) by 933 days.

(21) Appl. No.: 18/076,504

(22) Filed: Dec. 7, 2022

(65) Prior Publication Data

US 2023/0181808 A1 Jun. 15, 2023

Related U.S. Application Data

(60) Provisional application No. 63/287,692, filed on Dec. 9, 2021.

(51) Int. Cl.

*A61M 1/36* (2006.01)

*B04B 13/00* (2006.01)

(52) U.S. Cl.

CPC ........... *A61M 1/3696* (2014.02); *B04B 13/00* (2013.01)

(58) Field of Classification Search

CPC ........ A61M 1/3696; A61M 2202/0415; A61M 2202/0429; A61M 2205/3306; A61M 2205/3334; A61M 2205/3365; A61M 2205/50; A61M 1/38; A61M 1/385; B04B 13/00

USPC .................................................. 494/4, 7, 10

See application file for complete search history.

(56) References Cited

U.S. PATENT DOCUMENTS

| | | | |
|---|---|---|---|
| 5,194,145 | A | 3/1993 | Schoendorfer |
| 5,316,667 | A | 5/1994 | Brown et al. |
| 5,632,893 | A | 5/1997 | Brown et al. |
| 5,868,696 | A | 2/1999 | Giesler et al. |
| 6,419,822 | B2 | 7/2002 | Muller et al. |
| 6,451,203 | B2 | 9/2002 | Brown |
| 8,075,468 | B2 | 12/2011 | Min et al. |

(Continued)

FOREIGN PATENT DOCUMENTS

WO WO 2018/053217 A1 3/2018

OTHER PUBLICATIONS

Extended European Search Report for European Patent Application No. 22211844.0, dated May 2, 2023.

*Primary Examiner* — Claire X Wang

*Assistant Examiner* — Shuyi S. Liu

(74) *Attorney, Agent, or Firm* — Cook Alex Ltd.

(57) ABSTRACT

A fluid processing device includes a controller, a centrifuge, and a pump system. The controller controls the pump system to convey a fluid into a centrifuge chamber received by the centrifuge at first and second rates, with the controller also controlling the centrifuge to rotate the chamber at a first rotation rate when the fluid is being conveyed into the chamber at the first rate and controlling the centrifuge to rotate the chamber at a second rotation rate when the fluid is being conveyed into the chamber at the second rate. The first and second rotation rates are different, with each being based at least in part on a concentration of a fluid component within the fluid, the rate at which the pump system is conveying the fluid into the centrifuge chamber, and a target concentration of the fluid component in one of the first and second constituents.

20 Claims, 10 Drawing Sheets

(56) References Cited

U.S. PATENT DOCUMENTS

| | | | | |
|---|---|---|---|---|
| 8,556,793 | B2 | 10/2013 | Foley et al. | |
| 2004/0230152 | A1* | 11/2004 | Bainbridge ..... | A61M 1/362262<br>210/782 |
| 2008/0200859 | A1* | 8/2008 | Hatamian ........... | A61M 60/284<br>604/6.02 |
| 2016/0339451 | A1* | 11/2016 | Meisberger .......... | C07D 403/10 |
| 2019/0369008 | A1 | 12/2019 | Kusters | |

* cited by examiner

SYSTEMS AND METHODS FOR SETTING A CONTINUOUS-FLOW CENTRIFUGE ROTATION RATE

CROSS-REFERENCE TO RELATED APPLICATIONS

This application claims the benefit of and priority of U.S. Provisional Patent Application Ser. No. 63/287,692, filed Dec. 9, 2021, the contents of which are incorporated by reference herein.

BACKGROUND

Field of the Disclosure

The present disclosure relates to continuous-flow centrifuges. More particularly, the present disclosure relates to setting a rotation rate for a continuous-flow centrifuge.

Description of Related Art

Various blood processing systems now make it possible to collect particular blood constituents, rather than whole blood, from a blood source. Typically, in such systems, whole blood is drawn from a source, the particular blood component or constituent is removed and collected, and the remaining blood constituents are returned to the source.

Whole blood is typically separated into its constituents through centrifugation. This requires that the whole blood be passed through a centrifuge after it is withdrawn from, and before it is returned to, the source. To avoid contamination and possible infection of the source, the blood is preferably contained within a sealed, sterile fluid flow circuit during the entire centrifugation process. Typical blood processing systems thus include a permanent, reusable centrifuge assembly containing the hardware (drive system, pumps, valve actuators, programmable controller, and the like) that spins and pumps the blood, and a disposable, sealed and sterile fluid flow circuit that is mounted in cooperation on the hardware. The centrifuge assembly engages and spins a disposable centrifuge chamber of the fluid flow circuit during a collection procedure. The blood, however, makes actual contact only with the fluid flow circuit, which assembly is used only once and then discarded.

As the whole blood is spun by the centrifuge, the heavier (greater specific gravity) components, such as red blood cells, move radially outwardly away from the center of rotation toward the outer or "high-g" wall of the separation chamber. The lighter (lower specific gravity) components, such as plasma, migrate toward the inner or "low-g" wall of the separation chamber. Various ones of these components can be selectively removed from the whole blood by forming appropriately located channeling seals and outlet ports in the separation chamber.

Separation efficiency and the hematocrit of a separated packed red blood cell product depend upon a number of factors, including the rate at which blood is conveyed into the centrifuge. For example, an increased inflow rate will result in a relatively low hematocrit at a given rotation rate. While it is typically preferred for the hematocrit to remain uniform throughout the course of a separation procedure, it is not uncommon for the flow rate of blood entering the centrifuge to vary throughout a procedure. The inflow rate may change for any of a number of reasons, including a change resulting from venous flow control for a living blood source (e.g., if the rate at which blood is drawn from a donor or patient must be temporarily reduced to avoid or reverse vein collapse), such that separation efficiency and the hematocrit of a separated packed red blood cell product may vary throughout a procedure when the rotation rate of the centrifuge remains constant. This may lead to inaccurate yields, inconsistent products, and longer procedure times. Accordingly, it would be advantageous to provide systems and methods in which the rotation rate of a centrifuge changes in response to a change in the rate at which blood is conveyed into the centrifuge during a separation procedure so as to maintain a substantially constant separation efficiency and red blood cell product hematocrit throughout the procedure.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a fluid processing device includes a controller and a centrifuge configured to receive and rotate a continuous-flow centrifuge chamber of a fluid flow circuit so as to separate a fluid in the centrifuge chamber into at least first and second constituents. The device also includes a pump system configured to convey the fluid through the fluid flow circuit and into the centrifuge chamber at first and second rates. The controller is configured to control the centrifuge to rotate the centrifuge chamber at a first rotation rate when the pump system is conveying the fluid into the centrifuge chamber at the first rate. The controller is further configured to control the centrifuge to rotate the centrifuge chamber at a second rotation rate when the pump system is conveying said fluid into the centrifuge chamber at the second rate. The first and second rotation rates are different, with each of the first and second rotation rates being based at least in part on a concentration of a fluid component within the fluid, the rate at which the pump system is conveying the fluid into the centrifuge chamber, and a target concentration of the fluid component in one of the first and second constituents.

In another aspect, a method of separating a fluid includes conveying the fluid into a continuous-flow centrifuge chamber of a fluid flow circuit at first and second rates and rotating the centrifuge chamber with a centrifuge so as to separate the fluid in the centrifuge chamber into at least first and second constituents. The centrifuge rotates the centrifuge chamber at a first rotation rate when the fluid is being conveyed into the centrifuge chamber at the first rate and at a different second rotation rate when the fluid is being conveyed into the centrifuge chamber at the second rate. Each of the first and second rotation rates is based at least in part on a concentration of a fluid component within the fluid, the rate at which the fluid is being into the centrifuge chamber, and a target concentration of the fluid component in one of the first and second constituents.

These and other aspects of the present subject matter are set forth in the following detailed description of the accompanying drawings.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

FIGS. 1-15 show components of a blood or fluid processing system that embodies various aspects of the present subject matter. While the system may be described herein in terms of its use in separating blood into two or more components, it should be understood that systems according to the present disclosure can be used for processing a variety of biological or bodily fluids (including fluids containing both bodily and non-bodily fluids, such as anticoagulated blood), as well as non-bodily fluids.

Figure 1:
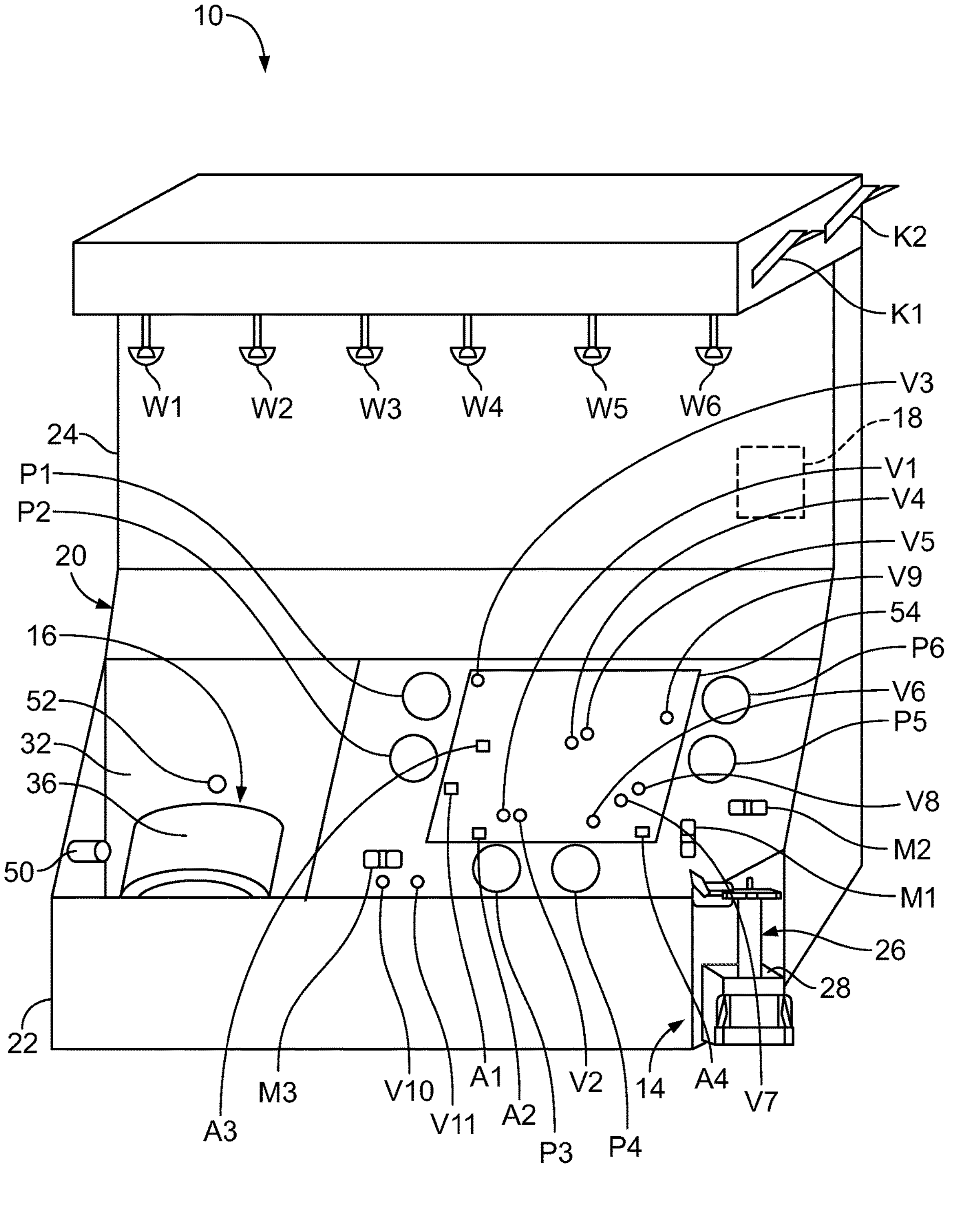
FIG. 1 is a perspective view of an exemplary fluid processing device that comprises a component of a fluid processing system according to an aspect of the present disclosure.
Figure 2:
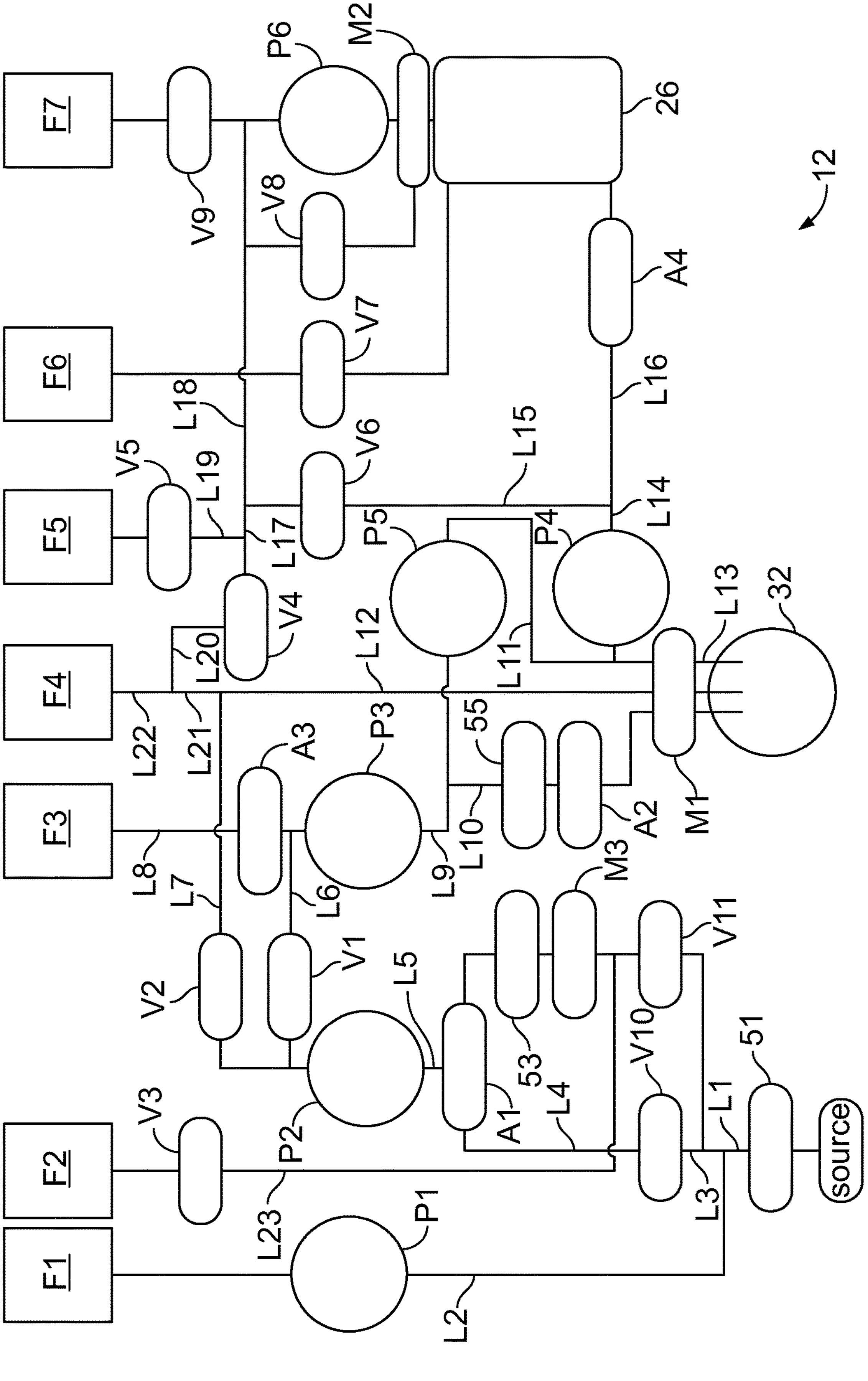
FIG. 2 is a schematic view of an exemplary disposable fluid flow circuit that may be mounted to the fluid processing device of FIG. 1 to complete a fluid processing system according to an aspect of the present disclosure.

Fluid processing systems according to the present disclosure typically include two principal components, a durable and reusable fluid processing device 10 (FIG. 1) and a disposable fluid flow circuit 12 (FIG. 2). The illustrated fluid processing device 10 includes a spinning membrane separator drive unit 14 (FIG. 1), a centrifuge or centrifugal separator 16 (FIG. 3), additional components that control fluid flow through the disposable flow circuit 12, and a controller 18 (FIG. 1), which governs the operation of the other components of the fluid processing device 10 to perform a procedure selected by the operator. The principles described herein regarding setting the rotation rate of a continuous-flow centrifuge are not limited to any particular fluid processing systems or procedures, so no complete fluid processing devices or procedures will be described in detail herein. However, reference may be made to PCT Patent Application Publication No. WO 2018/053217 A1 (which is hereby incorporated herein by reference) for a detailed description of the fluid processing device 10 of FIG. 1, along with various exemplary procedures that may be carried out using such a system.

I. The Durable Fluid Processing Device

The fluid processing device 10 (FIG. 1) is configured as a durable item that is capable of long-term use. It should be understood that the fluid processing device 10 of FIG. 1 is merely exemplary of one possible configuration and that fluid processing devices according to the present disclosure may be differently configured. For example, it is within the scope of the present disclosure for the fluid processing device to omit a spinning membrane separator drive unit 14.

In the illustrated embodiment, the fluid processing device 10 is embodied in a single housing or case 20. The illustrated case 20 includes a generally horizontal portion 22 (which may include an inclined or angled face or upper surface for enhanced visibility and ergonomics) and a generally vertical portion 24. The spinning membrane separator drive unit 14 and the centrifugal separator 16 are shown as being incorporated into the generally horizontal portion 22 of the case 20, while the controller 18 is shown as being incorporated into the generally vertical portion 24.

A. Spinning Membrane Separator Drive Unit

The illustrated fluid processing device 10 includes a spinner support or spinning membrane separator drive unit 14 (FIG. 1) for accommodating a generally cylindrical spinning membrane separator 26 of a fluid flow circuit 12 (FIG. 2). U.S. Pat. No. 5,194,145 (which is hereby incorporated herein by reference) describes an exemplary spinning membrane separator drive unit that would be suitable for incorporation into the fluid processing device 10, but it should be understood that the spinning membrane separator drive unit 14 may be differently configured without departing from the scope of the present disclosure. The principles described herein are specific to setting the rotation rate of the centrifugal separator 16, so the spinning membrane separator drive unit 14 is not described in detail herein.

B. Centrifugal Separator

Principles of setting the rotation rate of a continuous-flow centrifuge are described herein in the context of a particularly configured centrifugal separator 16 and associated continuous-flow centrifuge chamber or centrifugal separation chamber 32 for illustrative purposes, but it should be understood that such principles may be practiced in combination with differently configured centrifugal separators and/or continuous-flow centrifuge chambers, and that the principles described herein are not specific to the illustrated centrifuge chamber 32 and/or centrifugal separator 16.

Figure 3:
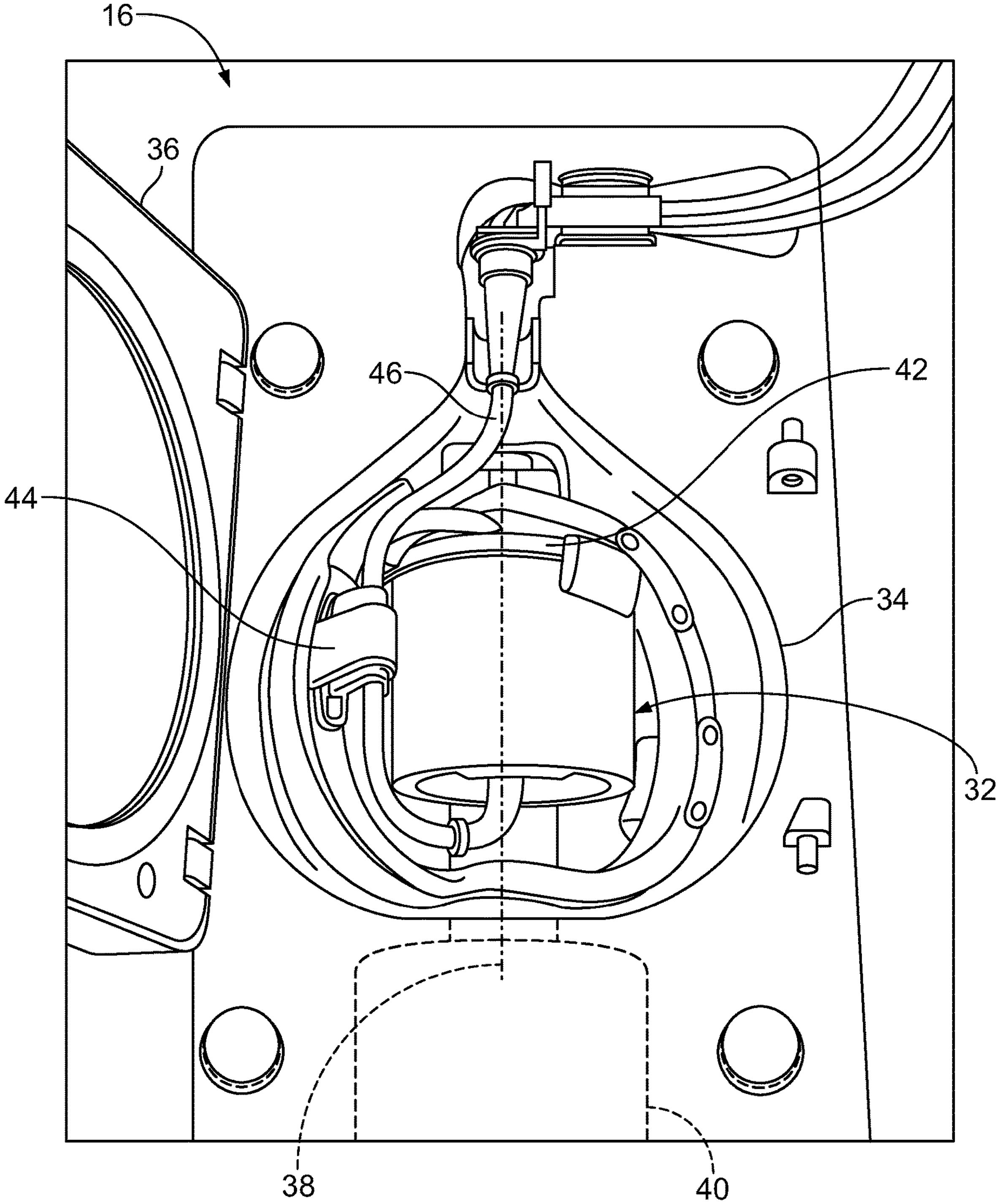
FIG. 3 is a perspective view of an exemplary centrifugal separator of the fluid processing device of FIG. 1, with the centrifuge chamber of a fluid flow circuit mounted therein.

The illustrated centrifugal separator 16 includes a centrifuge compartment 34 that may receive the other components of the centrifugal separator 16 (FIG. 3). The centrifuge compartment 34 may include a lid 36 that is opened to insert and remove a centrifuge chamber 32 of the fluid flow circuit 12. During a separation procedure, the lid 36 may be closed with the centrifuge chamber 32 positioned within the centrifuge compartment 34, as the centrifuge chamber 32 is spun or rotated about an axis 38 under the power of an electric drive motor or rotor 40 of the centrifugal separator 16.

Figure 4:
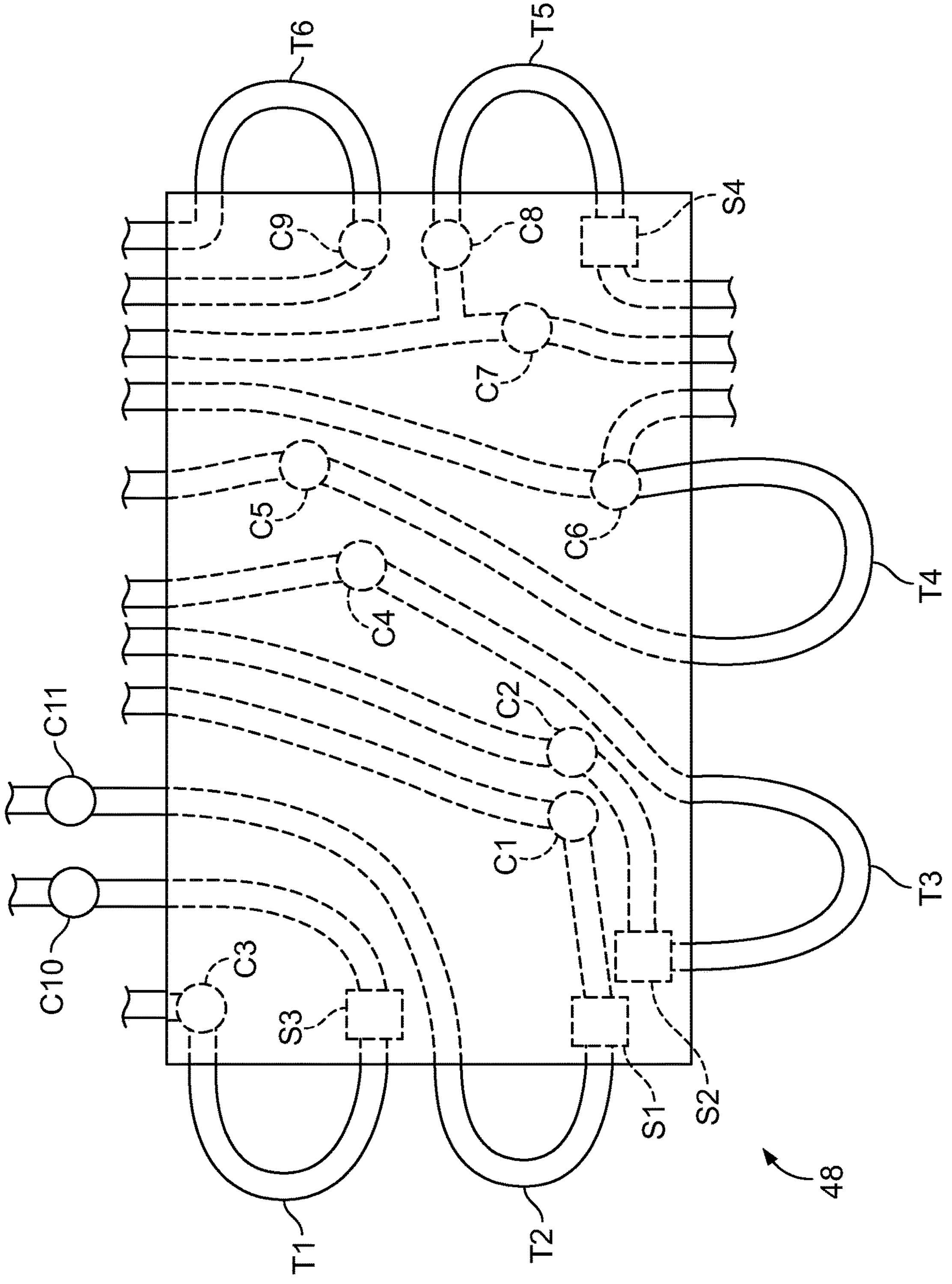
FIG. 4 is a top plan view of an exemplary cassette of a fluid flow circuit, which can be actuated to perform a variety of different fluid processing procedures in association with the fluid processing device shown in FIG. 1.

The particular configuration and operation of the centrifugal separator 16 depends upon the particular configuration of the centrifuge chamber 32 of the fluid flow circuit 12. In one embodiment, the centrifugal separator 16 is similar in structure and operation to that of the ALYX system manufactured by Fenwal, Inc. of Lake Zurich, Illinois, which is an affiliate of Fresenius Kabi AG of Bad Homburg, Germany, as described in greater detail in U.S. Pat. No. 8,075,468, which is hereby incorporated herein by reference. More particularly, the centrifugal separator 16 may include a carriage or support 42 that holds the centrifuge chamber 32 and a yoke member 44. The yoke member 44 engages an umbilicus 46 of the fluid flow circuit 12, which extends between the centrifuge chamber 32 and a cassette 48 of the fluid flow circuit 12 (FIG. 4). The yoke member 44 causes the umbilicus 46 to orbit around the centrifuge chamber 32 at a one omega rotational speed. The umbilicus 46 twists about its own axis as it orbits around the centrifuge chamber 32. The twisting of the umbilicus 46 about its axis as it rotates at one omega with the yoke member 44 imparts a two omega rotation to the centrifuge chamber 32, according to known design. The relative rotation of the yoke member 44 at a one omega rotational speed and the centrifuge chamber 32 at a two omega rotational speed keeps the umbilicus 46 untwisted, avoiding the need for rotating seals.

Figure 6:
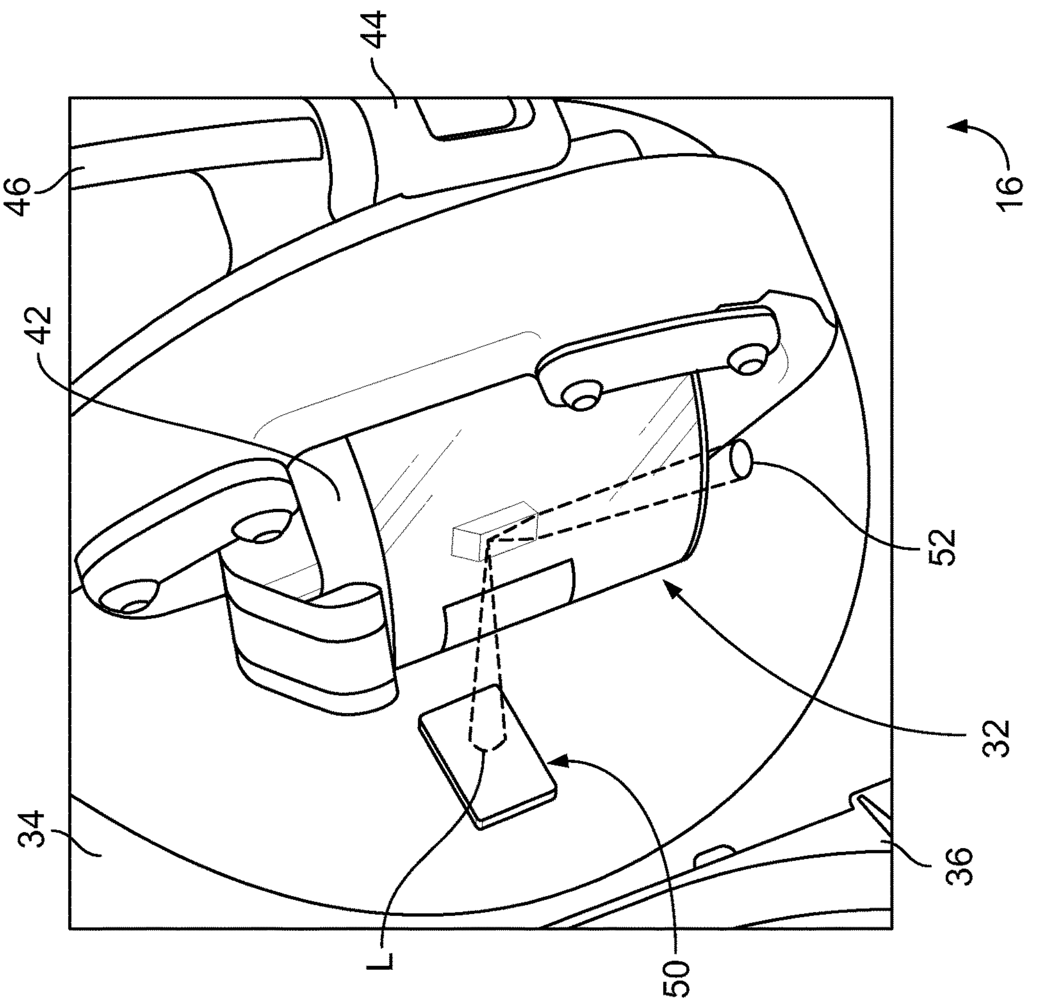
FIG. 6 is a perspective view of the centrifugal separator of FIG. 3, with the light source operating to transmit a light beam to a light detector of the interface monitoring assembly.
Figure 5:
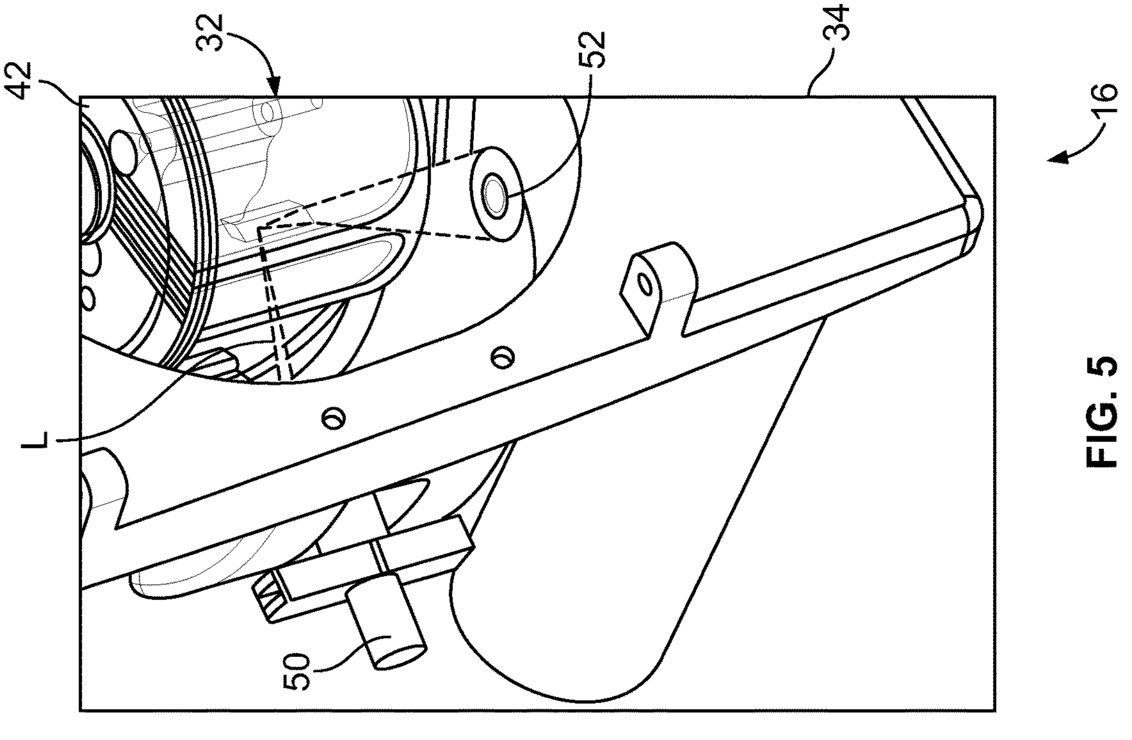
FIG. 5 is a perspective view of the centrifugal separator of FIG. 3, with selected portions thereof broken away to show a light source of an interface monitoring assembly.
Figure 7:
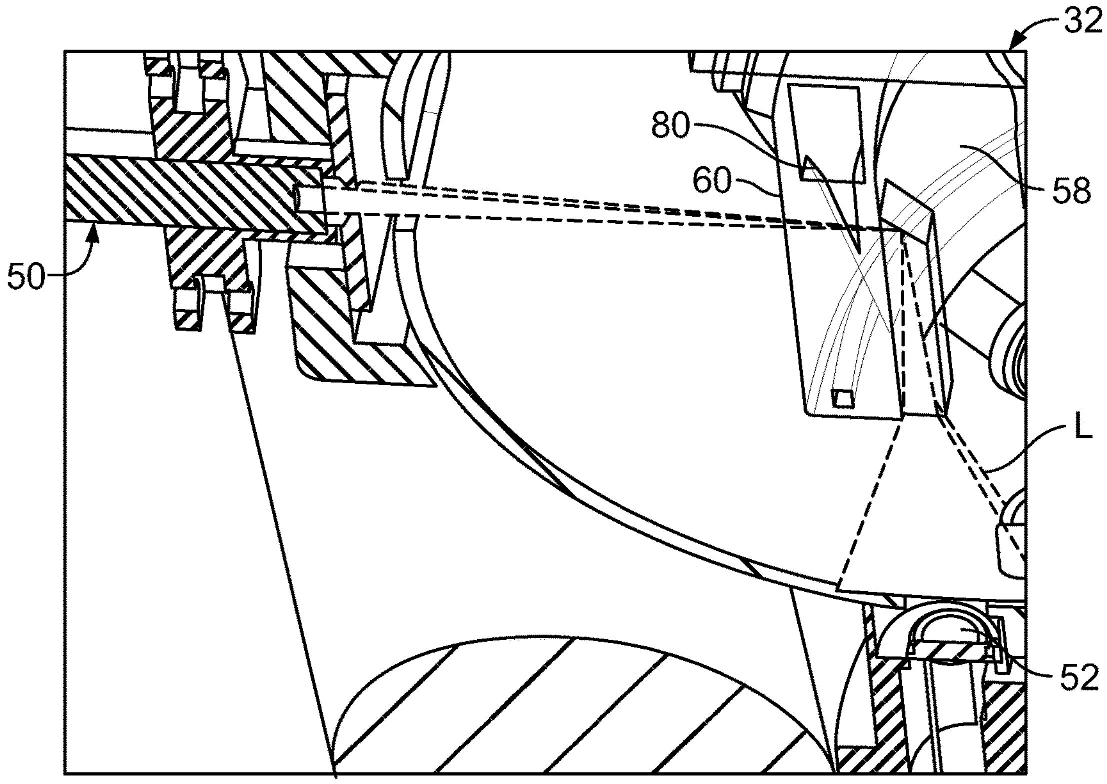
FIG. 7 is a perspective view of the centrifugal separator of FIG. 3, with selected portions thereof broken away to show the light source and light detector of the interface monitoring assembly.

A fluid is introduced into the centrifuge chamber 32 by the umbilicus 46, with the fluid being separated (e.g., into a layer of less dense components, such as platelet-rich plasma, if the fluid is blood, and a layer of more dense components, such as packed red blood cells, if the fluid is blood) within the centrifuge chamber 32 as a result of centrifugal forces as it rotates. Components of an interface monitoring assembly may be positioned within the centrifuge compartment 16 to oversee separation of fluid within the centrifuge chamber 32. As shown in FIGS. 5-7, the interface monitoring assembly may include a light source 50 and a light detector 52, which is positioned and oriented to receive at least a portion of the light emitted by the light source 50. The illustrated light source 50 and light detector 52 are associated with stationary surfaces of the centrifuge compartment 34, but either or both may instead be associated with a movable structure or component of the fluid processing device 10, as in U.S. Pat. No. 5,316,667, which is hereby incorporated herein by reference.

The orientation of the various components of the interface monitoring system depends at least in part on the particular configuration of the centrifuge chamber 32, which will be described in greater detail herein. In general, though, the light source 50 emits a light beam "L" (e.g., a laser light beam) through the separated fluid components within the centrifuge chamber 32 (which may be formed of a material that substantially transmits the light L or at least a particular wavelength of the light L without absorbing it). A portion of the light L reaches the light detector 52, which transmits a signal to the controller 18 that is indicative of the location of an interface between the separated fluid components. If the controller 18 determines that the interface is in the wrong location (which can affect the separation efficiency of the centrifugal separator 16 and/or the quality of the separated blood components), then it can issue commands to the appropriate components of the fluid processing device 10 to modify their operation so as to move the interface to the proper location.

C. Other Components of the Fluid Processing Device

In addition to the spinning membrane separator drive unit 14 and the centrifugal separator 16, the fluid processing device 10 may include other components compactly arranged to aid fluid processing.

The generally horizontal portion 22 of the case 20 of the illustrated fluid processing device 10 includes a cassette station 54, which accommodates a cassette 48 of the fluid flow circuit 12 (FIG. 4). In one embodiment, the cassette station 54 is similarly configured to the cassette station of U.S. Pat. No. 5,868,696 (which is incorporated herein by reference), but is adapted to include additional components and functionality. The illustrated cassette station 54 includes a plurality of clamps or valves V1-V9 (FIG. 1), which move between a plurality of positions (e.g., between a retracted or lowered position and an actuated or raised position) to selectively contact or otherwise interact with corresponding valve stations C1-C9 of the cassette 48 of the fluid flow circuit 12 (FIGS. 2 and 4). Depending on the configuration of the fluid flow circuit 12, its cassette 48 may not include a valve station C1-C9 for each valve V1-V9 of the cassette station 54, in which case fewer than all of the valves V1-V9 will be used in a separation procedure.

In the actuated position, a valve V1-V9 engages the associated valve station C1-C9 to prevent fluid flow through that valve station C1-C9 (e.g., by closing one or more ports associated with the valve station C1-C9, thereby preventing fluid flow through that port or ports). In the retracted position, a valve V1-V9 is disengaged from the associated valve station C1-C9 (or less forcefully contacts the associated valve station C1-C9 than when in the actuated position) to allow fluid flow through that valve station C1-C9 (e.g., by opening one or more ports associated with the valve station C1-C9, thereby allowing fluid flow through that port or ports). Additional clamps or valves V10 and V11 may be positioned outside of the cassette station 54 to interact with portions or valve stations C10 and C11 (which may be lengths of tubing) of the fluid flow circuit 12 to selectively allow and prevent fluid flow therethrough. The valves V1-V9 and corresponding valve stations C1-C9 of the cassette station 54 and cassette 48 may be differently configured and operate differently from the valves V10 and V11 and valve stations C10 and C11 that are spaced away from the cassette station 54.

The cassette station 54 may be provided with additional components, such as pressure sensors A1-A4, which interact with sensor stations S1-S4 of the cassette 48 to monitor the pressure at various locations of the fluid flow circuit 12. For example, if the fluid source is a human donor, one or more of the pressure sensors A1-A4 may be configured to monitor the pressure of the donor's vein during blood draw and return. Other pressure sensors A1-A4 may monitor the pressure of the spinning membrane separator 26 and the centrifuge chamber 32. The controller 18 may receive signals from the pressure sensor A1-A4 that are indicative of the pressure within the fluid flow circuit 12 and, if a signal indicates a low- or high-pressure condition, the controller 18 may initiate an alarm or error condition to alert an operator to the condition and/or to attempt to bring the pressure to an acceptable level without operator intervention.

The fluid processing device 10 may also include a plurality of pumps P1-P6 (which may be collectively referred to as a pump system) to cause fluid to flow through the fluid flow circuit 12. The pumps P1-P6 may be differently or similarly configured and/or function similarly or differently from each other. In the illustrated embodiment, the pumps P1-P6 are configured as peristaltic pumps, which may be generally configured as described in U.S. Pat. No. 5,868,696. Each pump P1-P6 engages a different tubing loop T1-T6 extending from a side surface of the cassette 48 (FIG. 4) and may be selectively operated under command of the controller 18 to cause fluid to flow through a portion of the fluid flow circuit 12, as will be described in greater detail. In one embodiment, all or a portion of the cassette station 54 may be capable of translational motion in and out of the case 20 to allow for automatic loading of the tubing loops T1-T6 into the associated pump P1-P6.

The illustrated fluid processing device 10 also includes an optical detection assembly or centrifugal separator sensor M1 for determining one or more properties of fluids flowing out of and/or into the centrifugal separator 16. If the fluid flowing out of the centrifugal separator 16 includes red blood cells, the centrifugal separator sensor M1 may be configured to determine the hematocrit of the fluid. If the fluid flowing out of the centrifugal separator 16 is platelet-rich plasma, the centrifugal separator sensor M1 may be configured to determine the platelet concentration of the platelet-rich plasma. The centrifugal separator sensor M1 may detect the one or more properties of a fluid by optically monitoring the fluid as it flows through tubing of the fluid flow circuit 12 or by any other suitable approach. The controller 18 may receive signals from the centrifugal separator sensor M1 that are indicative of the nature of flow into and out of the centrifuge separator 16 (e.g., whether air or a liquid flow is flowing through an inlet or outlet conduit connected to the centrifuge chamber 32, whether fluid is flowing through such conduit or is stagnant, etc.) and use the signals to optimize the separation procedure. If one or more properties of a fluid flowing into or out of the centrifuge chamber 32 is outside of an acceptable range, then the controller 18 may initiate an alarm or error condition to alert an operator to the condition. Exemplary optical detection assemblies are described in U.S. Pat. No. 6,419,822 and U.S. Patent Application Publication No. 2019/0369008 (both of which are hereby incorporated herein by reference), but it should be understood that a different approach may also be employed for optically monitoring fluid flow into and out of the centrifugal separator 16.

The illustrated fluid processing device 10 further includes a spinner outlet sensor M2, which accommodates tubing of the fluid flow circuit 12 that flows a separated substance out of the spinning membrane separator 26. The spinner outlet sensor M2 monitors the substance to determine one or more properties of the substance, and may do so by optically monitoring the substance as it flows through the tubing or by any other suitable approach. In one embodiment, separated plasma flows through the tubing, in which case the spinner outlet sensor M2 may be configured to determine the amount of cellular blood components in the plasma and/or whether the plasma is hemolytic and/or lipemic. This may be done using an optical monitor of the type described in U.S. Pat. No. 8,556,793 (which is incorporated herein by reference) or by any other suitable device and/or method.

The illustrated fluid processing device 10 also includes an air detector M3 (e.g., an ultrasonic bubble detector), which accommodates tubing of the fluid flow circuit 12 that flows fluid to a recipient. It may be advantageous to prevent air from reaching the recipient, so the air detector M3 may transmit signals to the controller 18 that are indicative of the presence or absence of air in the tubing. If the signal is indicative of air being present in the tubing, the controller 18 may initiate an alarm or error condition to alert an operator to the condition and/or to take corrective action to prevent the air from reaching the recipient (e.g., by reversing the flow of fluid through the tubing or diverting flow to a vent location).

The generally vertical portion 24 of the case 18 may include a plurality of weight scales W1-W6 (six are shown, but more or fewer may be provided), each of which may support one or more fluid containers F1-F7 of the fluid flow circuit 12 (FIG. 2). The containers F1-F7 receive fluid components or waste products separated during processing or assorted non-biological fluids (e.g., priming fluids, intravenous fluids, or additive fluids). Each weight scale W1-W6 transmits to the controller 18 a signal that is indicative of the weight of the fluid within the associated container F1-F7 to track the change of weight during the course of a procedure. This allows the controller 18 to process the incremental weight changes to derive fluid processing volumes and flow rates and subsequently generate signals to control processing events based, at least in part, upon the derived processing volumes. For example, the controller 18 may diagnose leaks and obstructions in the fluid flow circuit 12 and alert an operator.

The illustrated case 20 is also provided with a plurality of hooks or supports K1 and K2 that may support various components of the fluid flow circuit 12 or other suitably sized and configured objects.

D. Controller

As described above, the fluid processing device 10 includes a controller 18, which is suitably configured and/or programmed to control operation of the fluid processing device 10. In one embodiment, the controller 18 comprises a main processing unit (MPU), which can comprise, e.g., a Pentium™ type microprocessor made by Intel Corporation, although other types of conventional microprocessors can be used. In one embodiment, the controller 18 may be mounted inside the generally vertical portion 24 of the case 20, adjacent to or incorporated into an operator interface station (e.g., a touchscreen). In other embodiments, the controller 18 and operator interface station may be associated with the generally horizontal portion 22 or may be incorporated into a separate device that is connected (either physically, by a cable or the like, or wirelessly) to the fluid processing device 10.

The controller 18 is configured and/or programmed to execute at least one fluid processing application but, more advantageously, is configured and/or programmed to execute a variety of different fluid processing applications. For example, the controller 18 may be configured and/or programmed to carry out one or more of the following: a double unit red blood cell collection procedure, a plasma collection procedure, a plasma/red blood cell collection procedure, a red blood cell/platelet/plasma collection procedure, a platelet collection procedure, a platelet/plasma collection procedure, and a mononuclear cell collection procedure. Additional or alternative procedure applications (e.g., plasma exchange, red blood cell exchange, and photopheresis) can be included without departing from the scope of the present disclosure.

More particularly, in carrying out any one of these fluid processing applications, the controller 18 is configured and/or programmed to control one or more of the following tasks: drawing fluid into a fluid flow circuit 12 mounted to the fluid processing device 10, conveying fluid through the fluid flow circuit 12 to a location for separation (i.e., into the spinning membrane separator 26 or the centrifuge chamber 32 of the fluid flow circuit 12), separating the fluid into two or more components as desired, and conveying the separated components into storage containers, to a second location for further separation (e.g., into whichever of the spinning membrane separator 26 and centrifuge chamber 32 that was not used in the initial separation stage), or to a recipient (which may be the source from which the fluid was originally drawn).

This may include instructing the spinning membrane separator drive unit 14 and/or the centrifugal separator 16 to operate at a particular rotational speed and instructing a pump to convey fluid through a portion of the fluid flow circuit 12 at a particular flow rate. Hence, while it may be described herein that a particular component of the fluid processing device 10 (e.g., the spinning membrane separator drive unit 14 or the centrifugal separator 16) performs a particular function, it should be understood that that component is being controlled by the controller 18 to perform that function.

Before, during, and after a procedure, the controller 18 may receive signals from various components of the fluid processing device 10 to monitor various aspects of the operation of the fluid processing device 10 and characteristics of the fluid and separated fluid components as they flow through the fluid flow circuit 12. If the operation of any of the components and/or one or more characteristics of the fluid or separated fluid components is outside of an acceptable range, then the controller 18 may initiate an alarm or error condition to alert the operator and/or take action to attempt to correct the condition. The appropriate corrective action will depend upon the particular error condition and may include action that is carried out with or without the involvement of an operator.

For example, the controller 18 may include an interface control module, which receives signals from the light detector 52 of the interface monitoring assembly and the centrifugal separator sensor M1. The signals that the controller 18 receives from the light detector 52 are indicative of the location of an interface between the separated fluid components within the centrifuge chamber 32, while the signals from the centrifugal separator sensor M1 indicate whether the target interface location should be adjusted. If the controller 18 determines that the interface is in the wrong location, then it can issue commands to the appropriate components of the fluid processing device 10 to modify their operation so as to move the interface to the proper location. For example, the controller 18 may instruct the pump system to cause fluid to flow into the centrifuge chamber 32 at a different rate and/or for a separated fluid component to be removed from the centrifuge chamber 32 at a different rate and/or for the centrifuge chamber 32 to be spun at a different speed by the centrifugal separator 16.

If provided, an operator interface station associated with the controller 18 allows the operator to view on a screen or display (in alpha-numeric format and/or as graphical images) information regarding the operation of the system. The operator interface station also allows the operator to select applications to be executed by the controller 18, as well as to change certain functions and performance criteria of the system. If configured as a touchscreen, the screen of the operator interface station can receive input from an operator via touch-activation. Otherwise, if the screen is not a touchscreen, then the operator interface station may receive input from an operator via a separate input device, such as a computer mouse or keyboard. It is also within the scope of the present disclosure for the operator interface station to receive input from both a touchscreen and a separate input device, such as a keypad.

II. The Disposable Fluid Flow Circuit

A. Overview

As for the fluid flow circuit or flow set 12 (FIG. 2), it is intended to be a sterile, single use, disposable item. Before beginning a given procedure, the operator loads various components of the fluid flow circuit 12 in the case 20 in association with the fluid processing device 10. The controller 18 implements the procedure based upon preset protocols, taking into account other input from the operator. Upon completing the procedure, the operator removes the fluid flow circuit 12 from association with the fluid processing device 10. The portions of the fluid flow circuit 12 holding the collected fluid component or components (e.g., collection containers or bags) are removed from the case 20 and retained for storage, immediate use, or further processing. The remainder of the fluid flow circuit 12 is removed from the case 20 and discarded.

A variety of different disposable fluid flow circuits may be used in combination with the fluid processing device 10, with the appropriate fluid flow circuit depending on the procedure to be carried out using the system. Generally speaking, though, the fluid flow circuit 12 includes a cassette 48 (FIG. 4) to which the other components of the fluid flow circuit 12 are connected by flexible tubing or conduits. The other components may include a plurality of fluid containers F1-F7 (for holding fluid to be processed, a separated fluid component, a priming fluid, or an additive solution, for example), one or more fluid source access devices (e.g., a connector for accessing fluid within a fluid container), a centrifuge chamber 32 (FIGS. 8-10), and (optionally) a spinning membrane separator 26.

FIG. 2 illustrates an exemplary fluid flow circuit 12 having a single fluid access device (e.g., a phlebotomy needle) for alternately drawing fluid into the fluid flow circuit 12 and conveying fluid out of the fluid flow circuit 12. It should be understood that the illustrated fluid flow circuit 12 is merely exemplary and that the principles described herein may be employed with differently configured fluid flow circuits. This may include fluid flow circuits having a pair of fluid access devices, with one dedicated to drawing fluid into the fluid flow circuit and other being dedicated to conveying fluid out of the fluid flow circuit.

B. Cassette And Tubing

The cassette 48 (FIG. 4) provides a centralized, programmable, integrated platform for all the pumping and many of the valving functions required for a given fluid processing procedure. In one embodiment, the cassette 48 is similarly configured to the cassette of U.S. Pat. No. 5,868,696, but is adapted to include additional components (e.g., more tubing loops T1-T6) and functionality.

In use, the cassette 48 is mounted to the cassette station 54 of the fluid processing device 10, with a flexible diaphragm of the cassette 48 placed into contact with the cassette station 54. The flexible diaphragm overlays an array of interior cavities formed by the body of the cassette 48. The different interior cavities define sensor stations S1-S4, valve stations C1-C9, and a plurality of flow paths or conduits. The side of the cassette 48 opposite the flexible diaphragm may be sealed by another flexible diaphragm or a rigid cover, thereby sealing fluid flow through the cassette 48 from the outside environment.

Each sensor station S1-S4 is aligned with an associated pressure sensor A1-A4 of the cassette station 54, with each pressure sensor A1-A4 capable of monitoring the pressure within the associated sensor station S1-S4. Each valve station C1-C9 is aligned with an associated valve V1-V9, and may define one or more ports that allow fluid communication between the valve station C1-C9 and another interior cavity of the cassette 48 (e.g., a flow path). As described above, each valve V1-V9 is movable under command of the controller 18 to move between a plurality of positions (e.g., between a retracted or lowered position and an actuated or raised position) to selectively contact the valve stations C1-C9 of the cassette 48. In the actuated position, a valve V1-V9 engages the associated valve station C1-C9 to close one or more of its ports to prevent fluid flow therethrough. In the retracted position, a valve V1-V9 is disengaged from the associated valve station C1-C9 (or less forcefully contacts the associated valve station C1-C9 than when in the actuated position) to open one or more ports associated with the valve station C1-C9, thereby allowing fluid flow therethrough.

As described, a plurality of tubing loops T1-T6 extend from the side surface of the cassette 48 to interact with pumps P1-P6 of the fluid processing device 10. In the illustrated embodiment, six tubing loops T1-T6 extend from the cassette 48 to be received by a different one of six pumps P1-P6, but in other embodiments, a procedure may not require use of all of the pumps P1-P6, in which case the cassette 48 may include fewer than six tubing loops. The different pumps P1-P6 may interact with the tubing loops T1-T6 of the cassette 48 to perform different tasks during a separation procedure, as will be described in greater detail. Certain procedures require fewer than all of the sensor stations, valve stations, and/or tubing loops illustrated in the exemplary cassette 48 of FIG. 4, such that it should be understood that the cassettes of different fluid flow circuits 12 may be differently configured (e.g., with fewer sensor stations, valve stations, and/or tubing loops) without departing from the scope of the present disclosure.

Additional tubing or conduits extend from the side surface of the cassette 48 to connect to the other components of the fluid flow circuit 12, such as the various fluid containers F1-F7, the spinning membrane separator 26, and the centrifuge chamber 32. The number and content of the various fluid containers F1-F7 depends upon the procedure for which the fluid flow circuit 12 is used, so they will be described in greater detail with respect to an exemplary procedure. The tubing connected to the centrifuge chamber 32 (which includes one inlet conduit and two outlet conduits) may be aggregated into an umbilicus 46 (FIG. 3) that is engaged by the yoke member 44 of the centrifugal separator 16 (as described above) to cause the umbilicus 46 to orbit around and spin or rotate the centrifuge chamber 32 during a separation procedure.

Various additional components may be incorporated into the tubing leading out of the cassette 48 or into one of the cavities of the cassette 48. For example, as shown in FIG. 2, a manual clamp 51 may be associated with a line or lines leading to the fluid source and/or fluid recipient, a return line filter 53 (e.g., a microaggregate filter) may be associated with a line leading to a fluid recipient, filters may be positioned upstream of one or more of the fluid containers to remove a substance (e.g., leukocytes) from a separated component (e.g., red blood cells) flowing into the fluid container, and/or an air trap 55 may be positioned on a line upstream of the centrifuge chamber 32.

C. Centrifuge Chamber

Figure 8:
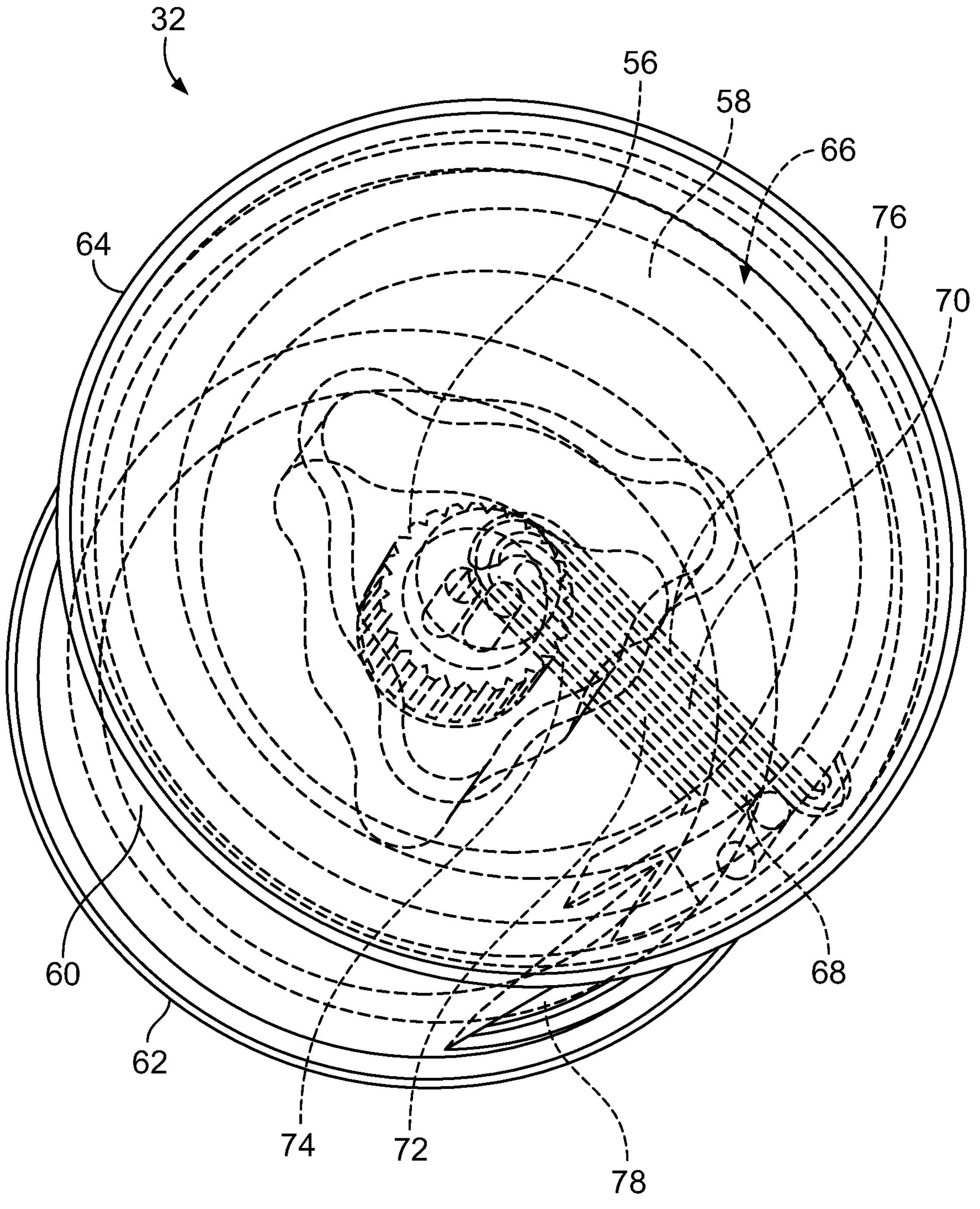
FIG. 8 is a perspective view of an exemplary centrifuge chamber of a fluid flow circuit.
Figure 9:
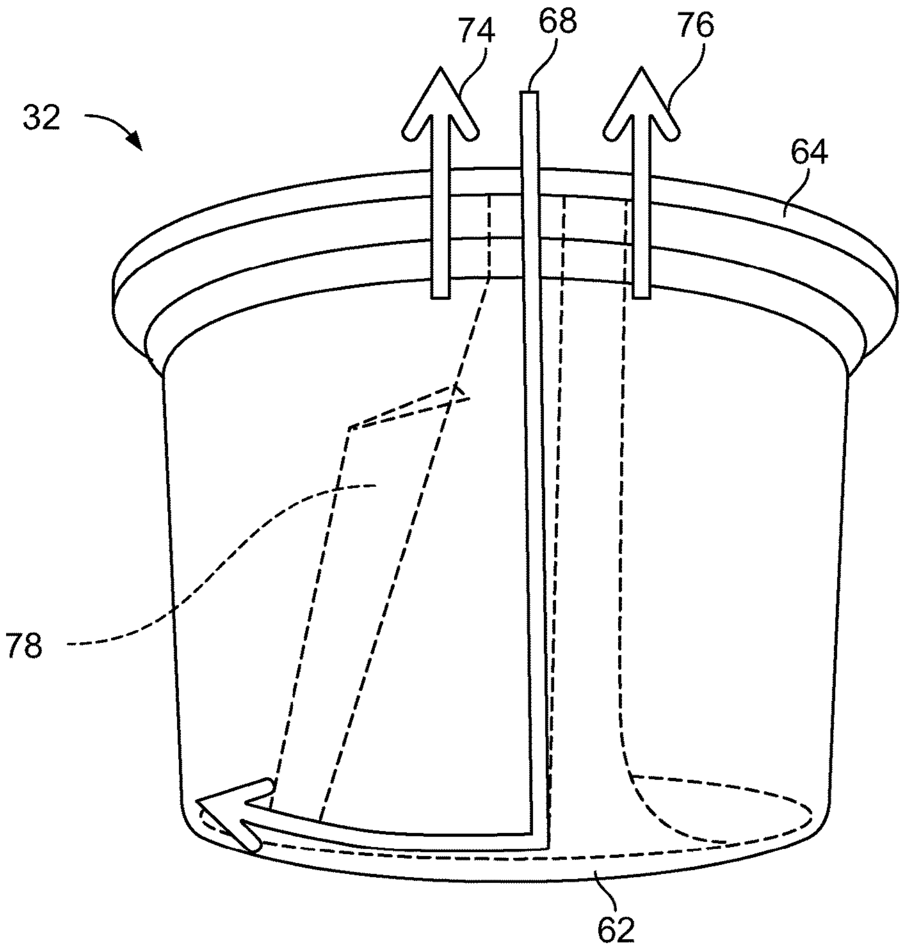
FIG. 9 is a front elevational view of the centrifuge chamber of FIG. 8.
Figure 10:
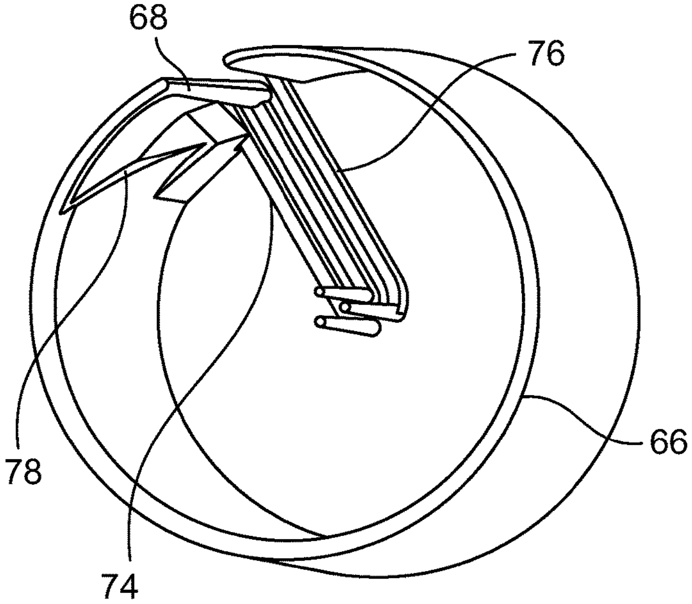
FIG. 10 is a bottom perspective view of the fluid flow path through the centrifuge chamber of FIG. 8.

An exemplary centrifuge chamber 32 is shown in FIGS. 8 and 9, while FIG. 10 illustrates the fluid flow path defined by the centrifuge chamber 32. In the illustrated embodiment, the body of the centrifuge chamber 32 is pre-formed in a desired shape and configuration (e.g., by injection molding) from a rigid, biocompatible plastic material, such as a non-plasticized medical grade acrylonitrile-butadiene-styrene (ABS). All contours, ports, channels, and walls that affect the fluid separation process are preformed in a single, injection molded operation. Alternatively, the centrifuge chamber 32 can be formed by separate molded parts, either by nesting cup-shaped subassemblies or two symmetric halves.

The underside of the centrifuge chamber 32 includes a shaped receptacle 56 that is suitable for receiving an end of the umbilicus 46 of the fluid flow circuit 12 (FIG. 3). A suitable receptacle 56 and the manner in which the umbilicus 46 may cooperate with the receptacle 56 to deliver fluid to and remove fluid from the centrifuge chamber 32 are described in greater detail in U.S. Pat. No. 8,075,468.

The illustrated centrifuge chamber 32 has radially spaced apart inner (low-g) and outer (high-g) side wall portions 58 and 60, a bottom or first end wall portion 62, and a cover or second end wall portion 64. The cover 64 comprises a simple flat part that can be easily welded or otherwise secured to the body of the centrifuge chamber 32. Because all features that affect the separation process are incorporated into one injection molded component, any tolerance differences between the cover 64 and the body of the centrifuge chamber 32 will not affect the separation efficiencies of the centrifuge chamber 32. The wall portions 58 and 60, the bottom 62, and the cover 64 together define an enclosed, generally annular channel 66 (FIG. 10).

An inlet 68 communicating with the channel 66 is defined between opposing interior radial walls 70 and 72. One of the interior walls 70 joins the outer (high-g) wall portion 60 and separates the upstream and downstream ends of the channel 66. The interior walls 70 and 72 define the inlet passageway 68 of the centrifuge chamber 32 which, in one flow configuration, allows fluid to flow from the umbilicus 46 to the upstream end of the channel 66.

The illustrated centrifuge chamber 32 further includes first and second outlets 74 and 76, respectively, which may be defined by opposing surfaces of interior radial walls. Both the first and second outlets 74 and 76 extend radially inward from the channel 66. The first (low-g) outlet 74 extends radially inward from an opening which, in the illustrated embodiment, is located at the inner side wall portion 58, while the second (high-g) outlet 76 extends radially inward from an opening that is associated with the outer side wall portion 60. The illustrated first outlet 74 is positioned adjacent to the inlet 68 (near the upstream end of the channel 66), while the second outlet 76 may be positioned at the opposite, downstream end of the channel 66.

It should be understood that the centrifuge chamber 32 illustrated in FIG. 8 is merely exemplary and that the centrifuge chamber 32 may be differently configured without departing from the scope of the present disclosure. For example, PCT Patent Application Publication No. WO 2018/053217 A1 describes other exemplary centrifuge chamber configurations that may be used in combination with the principles described herein.

III. Centrifugal Separation And Interface Detection Principles

Fluid flowed into the channel 66 separates into an optically dense layer "R" and a less optically dense layer "P" (FIGS. 11-13) as the centrifuge chamber 32 is rotated about the rotational axis 38. The optically dense layer R forms as larger and/or heavier fluid particles move under the influence of centrifugal force toward the outer (high-g) wall portion 60. If the fluid being separated is blood, the optically dense layer R will typically include red blood cells but, depending on the speed at which the centrifuge chamber 32 is rotated, other cellular components (e.g., larger white blood cells) may also be present in the optically dense layer R.

If the fluid being separated is blood, the less optically dense layer P typically includes a plasma constituent, such as platelet-rich plasma or platelet-poor plasma. Depending on the speed at which the centrifuge chamber 32 is rotated and the length of time that the blood is resident therein, other components (e.g., smaller white blood cells and anticoagulant) may also be present in the less optically dense layer P.

In one embodiment, fluid introduced into the channel 66 via the inlet 68 will travel in a generally clockwise direction (in the orientation of FIG. 8) as the optically dense layer R separates from the less optically dense layer P. The optically dense layer R continues moving in the clockwise direction as it travels the length of the channel 66 along the outer side wall portion 60, from the upstream end to the downstream end, where it exits the channel 66 via the second outlet 76. The less optically dense layer P separated from the optically dense layer R reverses direction, moving counterclockwise along the inner side wall portion 58 to the first outlet 74, adjacent to the inlet 68.

Figure 11:
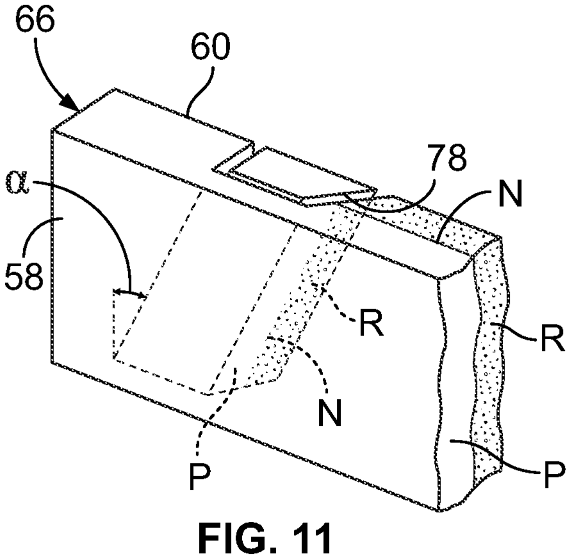
FIG. 11 is an enlarged perspective view of a portion of a channel of the centrifuge chamber of FIGS. 8-10, with an interface between separated fluid components being positioned at a (typically) desired location on a ramp defined within the channel.
Figure 12:
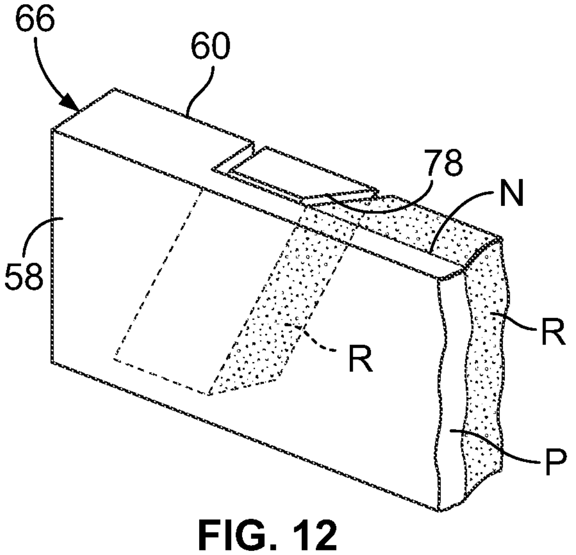
FIG. 12 is an enlarged perspective view of the channel and ramp of FIG. 11, with the interface being at a (typically) undesired high location on the ramp.
Figure 13:
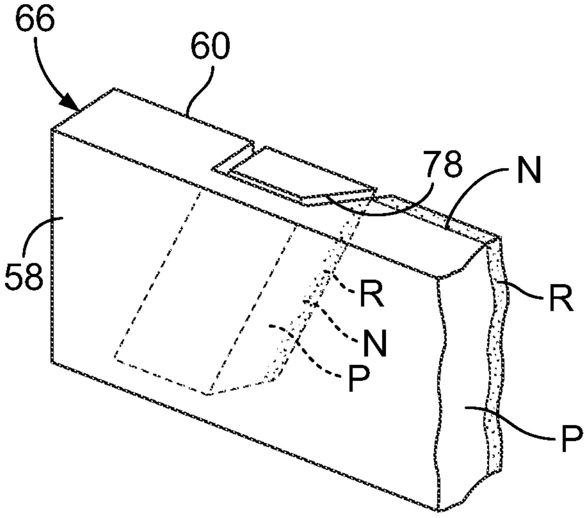
FIG. 13 is an enlarged perspective view of the channel and ramp of FIG. 11, with the interface being at a (typically) undesired low location on the ramp.

The transition between the optically dense layer R and the less optically dense layer P may be referred to as the interface "N". If the fluid being separated is blood, a buffy coat containing mononuclear cells and peripheral blood stem cells may be located at the interface N. The location of the interface N within the channel 66 of the centrifuge chamber 32 can dynamically shift during fluid processing, as FIGS. 11-13 show. If the location of the interface N is too high (that is, if it is too close to the inner side wall portion 58 and the first outlet 74, as in FIG. 12), red blood cells can flow into the first outlet 74, potentially adversely affecting the quality of the low density components (platelet-rich plasma or platelet-poor plasma). On the other hand, if the location of the interface N is too low (that is, if it resides too far away from the inner wall portion 58, as FIG. 13 shows), the collection efficiency of the system may be impaired. The ideal or target interface location may be experimentally determined, which may vary depending on any of a number of factors (e.g., the configuration of the centrifuge chamber 32, the rate at which the centrifuge chamber 32 is rotated about the rotational axis 38, etc.).

As described above, the fluid processing device 10 may include an interface monitoring assembly (including the light source 50 and the light detector 52), a centrifugal separator sensor M1, and a controller 18 with an interface control module to monitor and, as necessary, adjust or correct the position of the interface N. In the illustrated embodiment, the centrifuge chamber 32 is formed with a ramp 78 extending from the high-g wall portion 60 at an angle $\alpha$ across at least a portion of the channel 66 (FIGS. 8 and 11-13). The angle $\alpha$, measured with respect to the rotational axis 38 is about 25° in one embodiment. FIGS. 11-13 show the orientation of the ramp 78 when viewed from the low-g side wall portion 58 of the centrifuge chamber 32. Although it describes a flexible separation chamber, the general structure and function of the ramp 78 may be better understood with reference to U.S. Pat. No. 5,632,893, which is hereby incorporated herein by reference. The ramp 78 may be positioned at any of a number of locations between the upstream and downstream ends of the channel 66, but in one embodiment, the ramp 78 may be positioned generally adjacent to the first outlet 74, in the path of fluid and/or a fluid component moving from the inlet 68 to the first outlet 74.

The ramp 78 makes the interface N between the optically dense layer R and the less optically dense layer P more discernible for detection, displaying the optically dense layer R, less optically dense layer P, and interface N for viewing through a light-transmissive portion of the centrifuge chamber 32. To that end, the ramp 78 and at least the portion of the centrifuge chamber 32 angularly aligned with the ramp 78 may be formed of a light-transmissive material, although it may be advantageous for the entire centrifuge chamber 32 to be formed of the same light-transmissive material.

In the illustrated embodiment, the light source 50 of the interface monitoring system is associated with a fixture or wall of the centrifuge compartment 34 and oriented to emit a light L that is directed toward the rotational axis 38 of the centrifugal separator 16, as shown in FIGS. 5-7. If the light detector 52 is positioned at an angle with respect to the light source 50 (as in the illustrated embodiment), the light L emitted by the light source 50 must be redirected from its initial path before it will reach the light detector 52. In the illustrated embodiment, the light L is redirected by a reflector that is associated with a light-transmissive portion of the inner side wall portion 58, as shown in FIGS. 5 and 6. The reflector may be a separate piece that is secured to the inner side wall portion 58 (e.g., by being bonded thereto) or may be integrally formed with the body of the centrifuge chamber 66.

Figure 14:
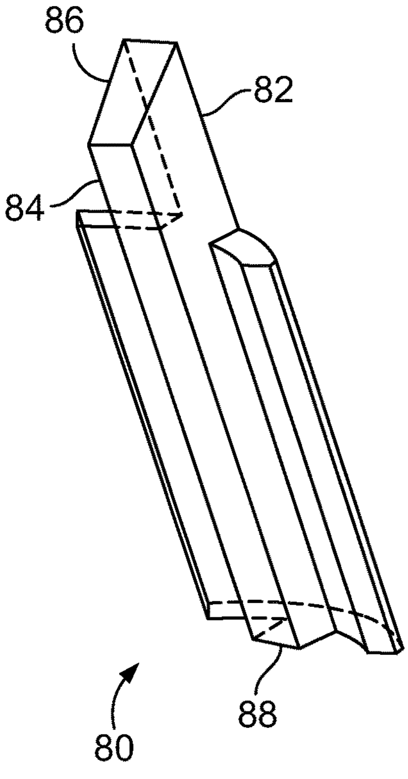
FIG. 14 is a perspective view of a prismatic reflector used in combination with the centrifuge chamber of FIGS. 8-10.

In one embodiment, the reflector may be a reflective surface, such as a mirror, that is oriented (e.g., at a 45° angle) to direct light L emitted by the light source 50 to the light detector 52. In another embodiment, the reflector is provided as a prismatic reflector 80 (FIGS. 7, 14, and 15), which is formed of a light-transmissive material (e.g., a clear plastic material) and has inner and outer walls 82 and 84 and first and second end walls 86 and 88 (FIG. 14). The inner wall 82 is positioned against the inner side wall portion 58 of the centrifuge chamber 32 and is oriented substantially perpendicular to the initial path of the light L from the light source 50. This allows light L from the light source 50 to enter into the prismatic reflector 80 via the inner wall 82 while continuing along its initial path. The light L continues through the prismatic reflector 80 along its initial path until it encounters the first end wall 86. The first end wall 86 is oriented at an angle (e.g., an approximately 45° angle) with respect to the inner wall 82 and the second end wall 88, causing the light L to be redirected within the prismatic reflector 80, rather than exiting the prismatic reflector 80 via the first end wall 86.

Figure 15:
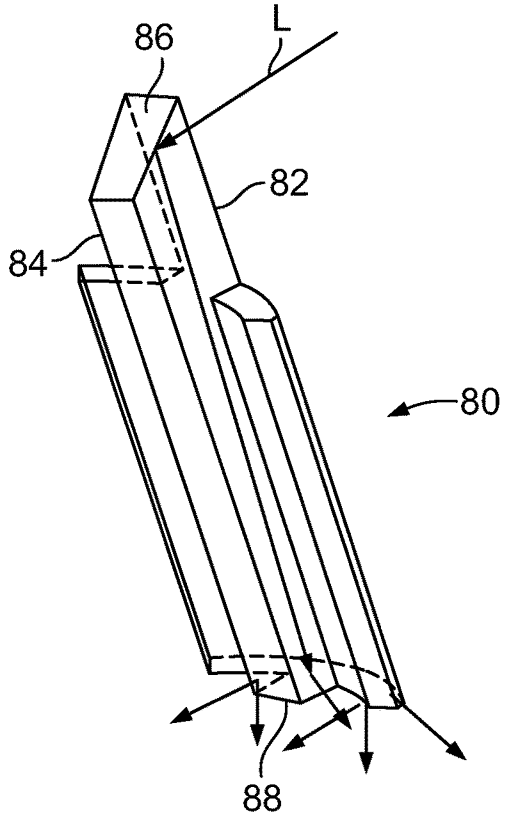
FIG. 15 is a perspective view of the prismatic reflector of FIG. 14, showing light being transmitted therethrough.

The first end wall 86 directs the light L at an angle to its initial path (which may be an approximately 90° angle, directing it from a path toward the rotational axis 38 to a path that is generally parallel to the rotational axis 38) toward the second end wall 88 (FIG. 15). The first end wall 86 and the inner and outer walls 82 and 84 of the prismatic reflector 80 may be configured to transmit the redirected light L from the first end wall 86 to the second end wall 88 by total internal reflection. The second end wall 88 is oriented substantially perpendicular to the redirected path of the light L through the prismatic reflector 80, such that the light L will exit the prismatic reflector 80 via the second end wall 88, continuing along its redirected path. In one embodiment, the second end wall 88 is roughened or textured or otherwise treated or conditioned to diffuse the light L as it exits the prismatic reflector 80, which may better ensure that the light L reaches the light detector 52 (FIG. 7).

The prismatic reflector 80 may be angularly aligned with the ramp 78, such that the light L from the light source 50 will only enter into the prismatic reflector 80 when the ramp 78 has been rotated into the path of the light L. At all other times (when the ramp 78 is not in the path of the light L), the light L will not reach the prismatic reflector 80 and, thus, will not reach the light detector 52.

Upon the ramp 78 first being rotated into the path of the light L from the light source 50, the light L will begin to reach the prismatic reflector 80, which directs the light L to the light detector 52. This causes the voltage output of the light detector 52 (i.e., the signal transmitted from the light detector 52 to the controller 18) to increase to a non-zero value or state. The ramp 78 and prismatic reflector 80 are eventually rotated out of alignment with the light source 50, at which time no light L will reach the prismatic reflector 80 and the voltage output of the light detector 52 will return to a low- or zero-state.

During the time that the ramp 78 and prismatic reflector 80 are rotated through the path of the light L from the light source 50, the light L continues through the channel 66 and the fluids in the channel 66. At least a portion of the light L (i.e., the portion not absorbed or reflected by the fluids) exits the channel 66 by striking and entering a light-transmissive portion of the inner side wall portion 58. The light L passes through the inner side wall portion 58 and enters the prismatic reflector 80, which redirects the light L from its initial path to the light detector 52, as described above.

The light detector 52 generates a signal that is transmitted to the interface control module of the controller 18, which can determine the location of the interface N on the ramp 78. In one embodiment, the location of the interface N is associated with a change in the amount of light L that is transmitted through the less optically dense layer P and the optically dense layer R. For example, the light source 50 may be configured to emit a light L that is more readily transmitted by platelet-rich plasma or platelet-poor plasma than by red blood cells, such as red visible light (from a laser or a differently configured light source L), which is substantially absorbed by red blood cells. The less optically dense layer P and the optically dense layer R each occupy a certain portion of the ramp 78, with the light detector 52 receiving different amounts of light L depending on whether the light L travels through the less optically dense layer P on the ramp 78 or the optically dense layer R on the ramp 78. The percentage of the ramp 78 occupied by each layer is related to the location of the interface N in the channel 66. Thus, by measuring the amount of time that the voltage output or signal from the light detector 52 is relatively high (corresponding to the time during which the light L is passing through only the less optically dense layer P on the ramp 78), the controller 18 may determine the location of the interface N and take steps to correct the location of the interface N, if necessary. An exemplary approach to adjustment of the position of the interface N is described in greater detail in PCT Patent Application Publication No. WO 2018/053217 A1.

IV. Setting Rotation Rate of Centrifugal Separator

Depending on the fluid separation objectives, there is a suitable procedure for separating and collecting any of a variety of different fluid components, either alone or in combination with other fluid components. Accordingly, prior to processing, an operator selects the desired protocol (e.g., using an operator interface station, if provided), which informs the controller 18 of the manner in which it is to control the other components of the fluid processing device 10 during the procedure.

The operator may also proceed to enter various parameters. In the case of blood separation, this may include information regarding the blood source, along with the target yield for the various blood components (which may also include entering a characteristic of the blood, such as a platelet pre-count) or some other collection control system (e.g., the amount of whole blood to be processed).

If there are any fluid containers (e.g., a storage solution container) that are not integrally formed with the fluid flow circuit 12, they may be connected to the fluid flow circuit 12 (e.g., by piercing a septum of a tube of the fluid flow circuit 12 or via a luer connector), with the fluid flow circuit 12 then being mounted to the fluid processing device 10 (including the fluid containers F1-F7 being hung from the weight scales W1-W6 and the hooks or supports H1 and H2, as appropriate). An integrity check of the fluid flow circuit 12 may be executed by the controller 18 to ensure the various components are properly connected and functioning.

Following a successful integrity check, the fluid flow circuit 12 is primed to move air contained in the various conduits and in the centrifuge chamber 32 into a more suitable location (e.g., a waste container). The selected procedure then commences, with fluid being conveyed into the fluid flow circuit 12 from a source and separated in the centrifuge chamber 32 within the centrifugal separator 16.

Conventionally, during a given stage of a multi-stage procedure, the centrifugal separator 16 will operate at a uniform or constant rotation rate to separate fluid in the centrifuge chamber 32 into two or more constituents. However, the rate at which fluid is conveyed into the centrifuge chamber 32 during an individual stage may vary, which will affect the separation efficiency of the fluid processing device 10. To avoid a change in separation efficiency, the rotation rate of the centrifugal separator 16 may be adjusted in response to a change in the rate at which fluid is pumped into the centrifuge chamber 32. In general, it has been found that a decrease in inflow rate is best addressed by a corresponding decrease in the rotation rate of the centrifugal separator 16 (with an increase in inflow rate being addressed by an increase in the rotation rate), but more precise controls are advantageous to ensure that separation efficiency remains substantially unaffected by a change in inflow rate.

More particularly, the rotation rate per minute ("RPM") of a continuous flow centrifuge determines the centrifugal g-force applied to a fluid within the centrifuge, based on the following relationships:

$$g=1.118\times10^{-5}*RPM^2*r \qquad [1] \text{ and}$$

$$RPM=\sqrt{\frac{g}{(1.118\times10^{-5})\times r}}, \qquad [2]$$

where g is the acceleration or g-force and r is the radius of the centrifuge.

The g-force is an important aspect in the determination of separation efficiency and may be one of the few parameters controllable by the fluid processing device 10. The following two relationships govern the separation efficiency of a continuous flow centrifuge separating whole blood into packed red blood cells and platelet-rich plasma:

$$\text{Efficiency} = \frac{H_{RBC} - H_{WB}}{H_{RBC}(1 - H_{WB})} \text{ and} \quad [3]$$

$$H_{RBC} = 0.948 - \frac{\beta Q_{WB} H_{WB}}{0.506 g A_{sep} S_{RBC}}, \quad [4]$$

where $H_{RBC}$ is the hematocrit of the packed red blood cells exiting the centrifuge, $H_{WB}$ is the hematocrit of the whole blood being pumped into the centrifuge, β is a shear sensitive constant, $Q_{WB}$ is the inlet flow rate, $A_{sep}$ is the separation area of the centrifuge, and $S_{RBC}$ is the sedimentation coefficient of red blood cells. It should be understood that β and $S_{RBC}$ may depend on a variety of factors (which are familiar to those of ordinary skill in the art), but in one exemplary embodiment described in greater detail in U.S. Pat. No. 6,451,203 (which is hereby incorporated herein by reference), the quantity $\beta/S_{RBC}$ may be expressed as $15.8\times10^6$ $s^{-1}$.

While the relationships of Equations [3] and [4] are presented in the context of blood separation, it should be understood that they may be generalized to separation of other types of fluid. For example, $H_{RBC}$ may be replaced by the target concentration of a fluid component in a fluid constituent exiting the centrifuge, with $H_{WB}$ being replaced by the concentration of that fluid component in the fluid being conveyed into the centrifuge, and $S_{RBC}$ being replaced by the sedimentation coefficient of that fluid component.

The variables of most importance in this analysis tend to be the inlet flow rate ($Q_{WB}$) and the g-force (g), which act inversely to one another. Typically, the other variables will remain constant throughout a procedure but, if not, changes may be accounted for by updating the variable(s).

As determined by the above relationships, if the g-force is held constant, then any changes in the inlet flow rate will have a direct impact on the hematocrit of the packed red blood cells exiting the centrifuge and, thus, on the plasma separation efficiency. Therefore, in conventional devices which maintain a standard constant centrifuge rotation rate RPM across procedures, any changes of the inlet flow rate will alter the efficiency of the centrifuge, with significant increases in inflow rate (as may occur in double-needle procedures) significantly decreasing efficiency. In the case of a procedure in which blood is separated into platelet-rich plasma and packed red blood cells, this may lead to inconsistent platelet yields and red blood cell product hematocrit. Therefore, an approach that applies the above relationships to enable adaption of the centrifuge rotation rate in response to inflow rate changes will allow for substantially constant separation efficiencies and outlet hematocrit, leading to more consistent products and faster procedure times.

Rearranging Equation [4] to solve for g yields Equation [5]:

$$g = \frac{\beta Q_{WB} H_{WB}}{0.506 A_{sep} S_{RBC} (0.948 H_{RBC})}. \quad [5]$$

A constant desired or target $H_{RBC}$ (which may be predetermined or user defined) may be employed, in which case, as the inlet flow rate Owe changes, the required g-force will change accordingly. The g-force output from Equation [5] can then be inserted into Equation [2] to determine the centrifuge rotation rate RPM required to ensure that a constant packed red blood cell hematocrit $H_{RBC}$ and, thus, separation efficiency (per Equation [3]) is achieved.

Any method involving changes to the centrifuge rotation rate during a procedure must also consider the impact of rotation rate changes in the interface monitoring assembly, if employed. For example, in the exemplary embodiment described above, light L from a light source 50 may only enter into a prismatic reflector 80 and be directed to a light detector 52 when a ramp 78 angularly aligned with the prismatic reflector 80 has been rotated into the path of the light L. During the time that the ramp 78 and prismatic reflector 80 are rotated through the path of the light L from the light source 50, the light L continues through the channel 66 and the fluids in the channel 66. In the case of blood separation, the light source 50 may be configured to emit a light L that is more readily transmitted by platelet-rich plasma or platelet-poor plasma than by red blood cells, such as red visible light. The plasma layer and the red blood cell layer each occupy a certain portion of the ramp 78, with the light detector 52 receiving different amounts of light L depending on whether the light L travels through the plasma layer on the ramp 78 or the red blood cell layer on the ramp 78. The percentage of the ramp 78 occupied by each layer is indicative of the radial position of the interface in the channel 66. Thus, by measuring the amount of time that the voltage output or signal from the light detector 52 is relatively high (which corresponds to the time during which the light L is passing through only the plasma layer on the ramp 78 and which may be referred to as the "pulse width" of the signal), the controller 18 may determine the radial position of the interface within the channel 66.

The amount of time that the prismatic reflector 80 is in the path of the light L during each rotation of the centrifuge will depend upon the rotation rate of the centrifuge. Thus, when the controller 18 is configured to adjust the rotation rate of the centrifuge in response to a change in fluid inflow rate, the controller 18 must know both the total length of time that the prismatic reflector 80 is in the path of the light L during each rotation of the centrifuge and the pulse width to determine the percentage of the ramp 78 occupied by each layer and, hence, the radial position of the interface. In particular, faster centrifuge rotation rates will lead to shorter signal pulse widths due to the following relationship:

$$\text{Pulse Width} = \frac{60 * \text{Open Window Circumference}}{\textit{Cent RPM} * \text{Chamber Circumference}}, \quad [6]$$

in which Open Window Circumference is the width or angular extent of the first end wall 86 of the prismatic reflector 80 (which is the portion of the prismatic reflector 80 that is configured to direct light L to the light detector 52) and Chamber Circumference is the circumference of the inner side wall portion 58 (i.e., the circumference of the centrifuge chamber 32 at the same radial position at which Open Window Circumference is measured). Accordingly, it will be seen that Equation [6] is indicative of the percentage of each rotation of the centrifuge during which light L can possibly be directed to the light detector 52 by the prismatic reflector 80.

In the embodiment presented herein, interface position is determined according to the following relationship:

$$\text{Interface Position (\%)} = \frac{\text{Saline Calibration Pulse Width} - \text{Current Plasma Pulse Width}}{\text{Saline Calibration Pulse Width}} \quad [7]$$

in which Saline Calibration Pulse Width is the maximum possible pulse width of a signal that may be transmitted by the light detector 52 (e.g., when only saline is in the channel 66) and Current Plasma Pulse Width is the output of Equation [6]. It will be seen that, if the centrifuge rotation rate were increased during separation without taking into account the decreasing total time during each rotation when light L can possibly be directed to the light source 52, then a smaller pulse width would be interpreted as a change in the radial position of the interface, rather than being understood as simply reflecting the change in the centrifuge rotation rate. The same would be true for a decrease of the centrifuge rotation rate.

Thus, to account for centrifuge rotation rate changes in the calculation of the Interface Position using Equation [7], Saline Calibration Pulse Width (which is a reference signal typically taken at the start of a procedure) must be updated in accordance with RPM changes. Saline Calibration Pulse Width is used to determine the baseline width (circumference in time) of the prismatic reflector 80 through which the optical signal is measured and accounts for any tolerance discrepancies in the centrifuge chamber 32 that may not be considered by simply using Equation [6] to calculate Saline Calibration Pulse Width with a standard or presumed Open Window Circumference based on designed dimensions of the prismatic reflector 80. It is again emphasized that, while reference is made to a specifically configured centrifuge chamber 32 and prismatic reflector 80, these same principals may be applied to differently configured centrifuge chambers and optical monitoring assemblies.

It is possible to update Saline Calibration Pulse Width with respect to centrifuge rotation rate RPM changes by using a theoretical calculation of Equation [6] as a baseline, where Open Window Circumference would be a constant based on the intended design dimensions. To account for any potential tolerance issues that may alter Open Window Circumference from the designed dimension, Equation [6] may be rearranged as follows:

$$\text{Open Saline Window Circumference} = \frac{\mathit{Cent\ RPM} * \text{Chamber Circumference} * \text{Saline Calibration Pulse Width}}{60}, \quad [8]$$

which can be used to determine the actual Open Saline Window Circumference based on the Saline Calibration Pulse Width measured at the start of the procedure. Then, throughout the procedure as the centrifuge rotation rate RPM changes, Saline Calibration Pulse Width Per RPM may be calculated as follows:

$$\text{Saline Calibration Pulse Width Per } \mathit{RPM} = \frac{60 * \text{Open Saline Window Circumference}}{\mathit{Cent\ RPM} * \text{Chamber Circumference}}, \quad [9]$$

and subsequently used in the calculation of Interface Position as follows:

$$\text{Interface Position (\%)} = \frac{\text{Saline Calibration Pulse Width Per } \mathit{RPM} - \text{Current Plasma Pulse Width}}{\text{Saline Calibration Pulse Width Per } \mathit{RPM}} \times 100, \quad [10]$$

which is a variation of Equation [7].

Figure 16:
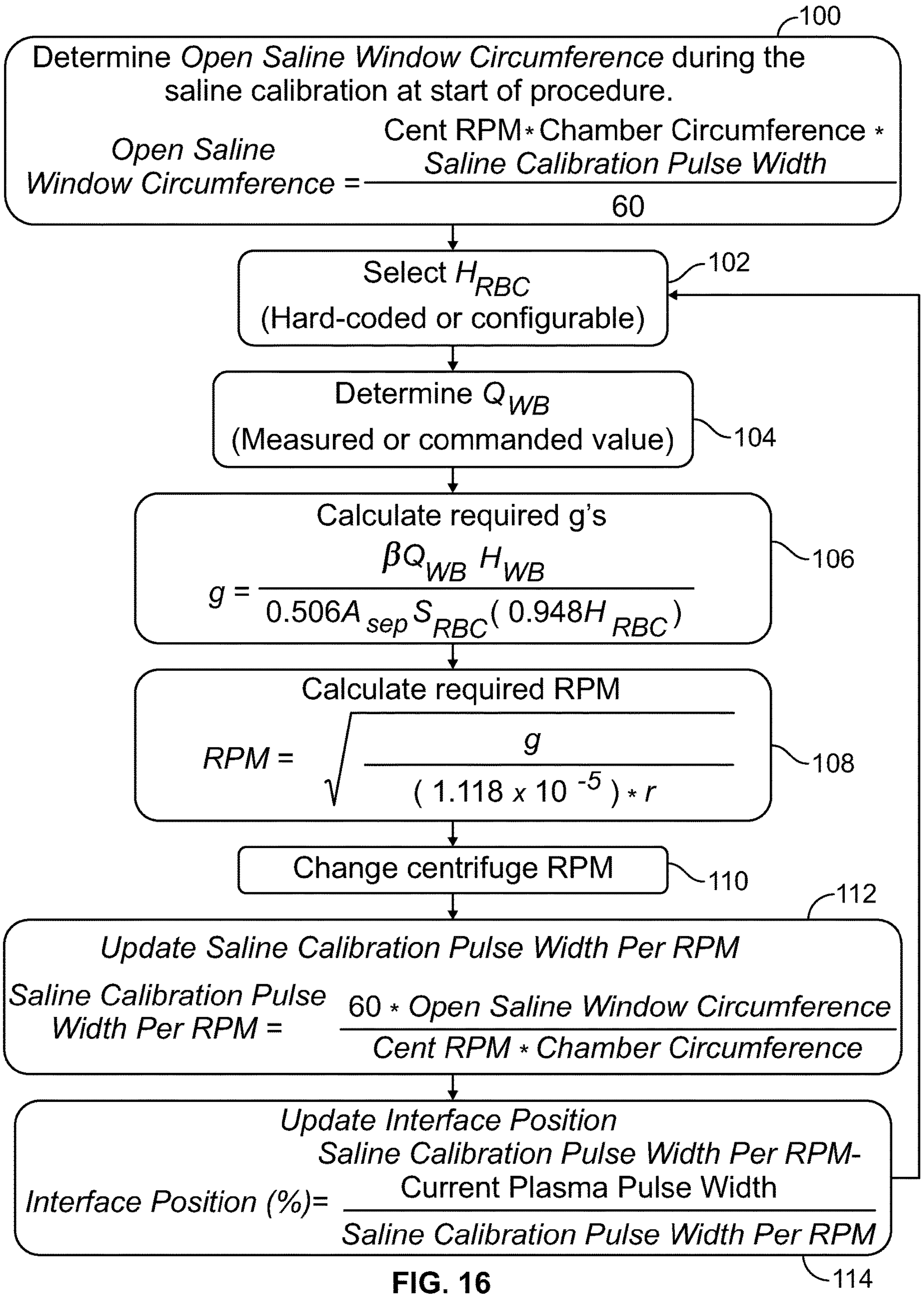
FIG. 16 is a flowchart of an exemplary approach to setting the rotation rate of a centrifuge according to an aspect of the present disclosure.

FIG. 16 illustrates an application of this approach to adjusting centrifuge rotation rate in response to a change in fluid inflow rate for a procedure in which blood is separated into packed red blood cells and a plasma constituent (e.g., platelet-rich plasma). As explained above, $H_{RBC}$ and $H_{WB}$ will typically remain uniform throughout the course of a procedure and are treated as constants when determining the appropriate centrifuge rotation rate change to implement in response to a change in fluid inflow rate. However, when one or both of $H_{RBC}$ and $H_{WB}$ are subject to change during a procedure, they may be updated at the appropriate times.

During an early stage of a procedure (which may be during a priming stage, for example), Equation [8] is employed by the controller 18 to determine Open Saline Window Circumference (indicated in FIG. 16 at step 100). $H_{RBC}$ and Owe are then determined (at steps 102 and 104, respectively), with $H_{RBC}$ being either determined based on the selected procedure or configurable (e.g., being selected by an operator or calculated by the controller 18) and $Q_{WB}$ being either measured or known in view of the selected procedure.

With that information, the controller 18 employs Equation [5] (at step 106 of FIG. 16) to determine the g-forces required to achieve $H_{RBC}$. The controller 18 then determines the centrifuge rotation rate RPM required to apply the calculated g-forces using Equation [2] (at step 108 of FIG. 16). The controller 18 commands the centrifugal separator 16 to rotate at the calculated rotation rate RPM (at step 110 of FIG. 16).

When the centrifugal separator 16 has been commanded to operate at the calculated rotation rate RPM, the controller 18 updates Saline Calibration Pulse Width Per RPM using Equation [9] (at step 112 of FIG. 16) and then updates Interface Position using Equation [10] (at step 114 of FIG. 16). The controller 18 may then return to step 102 to determine whether $H_{RBC}$ is to be updated and the process is repeated to ensure that any subsequent change in $Q_{WB}$ is addressed by a corresponding change in centrifuge rotation rate RPM, along with Saline Calibration Pulse Width Per RPM and Interface Position being similarly updated.

Again, it should be understood that the principles described herein are not limited to use with any particular centrifugation procedure or any particular fluid to be separated. Additionally, while particularly configured centrifuge chambers and centrifugal separators are shown and described in detail herein, it should be understood that the principles described herein are applicable to differently configured continuous-flow centrifuge chambers and centrifugal separators.

Aspects

Aspect 1. A fluid processing device, comprising: a controller; a centrifuge configured to receive and rotate a continuous-flow centrifuge chamber of a fluid flow circuit so as to separate a fluid in the centrifuge chamber into at least first and second constituents; and a pump system configured to convey said fluid through the fluid flow circuit and into the centrifuge chamber at first and second rates, wherein the controller is configured to control the centrifuge to rotate the centrifuge chamber at a first rotation rate when the pump system is conveying said fluid into the centrifuge chamber at the first rate, the controller is configured to control the centrifuge to rotate the centrifuge chamber at a second rotation rate when the pump system is conveying said fluid into the centrifuge chamber at the second rate, and said first and second rotation rates are different, with each of the first and second rotation rates being based at least in part on a concentration of a fluid component within the fluid, the rate at which the pump system is conveying said fluid into the centrifuge chamber, and a target concentration of the fluid component in one of said first and second constituents.

Aspect 2. The fluid processing device of Aspect 1, wherein said fluid comprises whole blood, one of said first and second constituents comprises packed red blood cells, said fluid component comprises red blood cells, and said target concentration of the fluid component in said one of said first and second constituents comprises a target hematocrit of the packed red blood cells.

Aspect 3. The fluid processing device of any one of the preceding Aspects, wherein the controller is configured to control the pump system to draw said fluid into the fluid flow circuit and to convey at least a portion of a separated fluid constituent out of the fluid flow circuit via a single fluid access device.

Aspect 4. The fluid processing device of any one of Aspects 1-2, wherein the controller is configured to control the pump system to draw said fluid into the fluid flow circuit via a first fluid access device and to convey at least a portion of a separated fluid constituent out of the fluid flow circuit via a second fluid access device.

Aspect 5. The fluid processing device of any one of the preceding Aspects, wherein said concentration of the fluid component within the fluid is substantially constant.

Aspect 6. The fluid processing device of any one of Aspects 1-4, wherein said target concentration of the fluid component in said one of said first and second constituents is substantially constant.

Aspect 7. The fluid processing device of any one of Aspects 1-4, wherein said concentration of the fluid component within the fluid and said target concentration of the fluid component in said one of said first and second constituents are substantially constant.

Aspect 8. The fluid processing device of any one of the preceding Aspects, wherein the controller is configured to control the pump system to convey said fluid through the fluid flow circuit and into the centrifuge chamber at said first and second rates during a single stage of a multi-stage separation procedure.

Aspect 9. The fluid processing device of Aspect 8, further comprising an interface monitoring assembly configured to transmit a first signal to the controller indicative of a first radial position of an interface between separated fluid constituents within the centrifuge chamber while said fluid is being conveyed into the centrifuge chamber at the first rate during said single stage of said multi-stage separation procedure and to transmit a second signal to the controller indicative of a second radial position of the interface between separated fluid constituents within the centrifuge chamber while said fluid is being conveyed into the centrifuge chamber at the second rate during said single stage of said multi-stage separation procedure, wherein the controller is configured to determine the first radial position of said interface based at least in part on the first signal and on the first rotation rate and to determine the second radial position of said interface based at least in part on the second signal and on the second rotation rate.

Aspect 10. The fluid processing device of any one of the preceding Aspects, wherein the first rate is greater than the second rate and the first rotation rate is greater than the second rotation rate.

Aspect 11. A method of separating a fluid, comprising: conveying a fluid into a continuous-flow centrifuge chamber of a fluid flow circuit at first and second rates; and rotating the centrifuge chamber with a centrifuge so as to separate the fluid in the centrifuge chamber into at least first and second constituents, with the centrifuge rotating the centrifuge chamber at a first rotation rate when the fluid is being conveyed into the centrifuge chamber at the first rate and at a second rotation rate when the fluid is being conveyed into the centrifuge chamber at the second rate, wherein said first and second rotation rates are different, with each of the first and second rotation rates being based at least in part on a concentration of a fluid component within the fluid, the rate at which the fluid is being into the centrifuge chamber, and a target concentration of the fluid component in one of said first and second constituents.

Aspect 12. The method of Aspect 11, wherein said fluid comprises whole blood, one of said first and second constituents comprises packed red blood cells, said fluid component comprises red blood cells, and said target concentration of the fluid component in said one of said first and second constituents comprises a target hematocrit of the packed red blood cells.

Aspect 13. The method of any one of Aspects 11-12, wherein said fluid is drawn into the fluid flow circuit and at least a portion of a separated fluid constituent is conveyed out of the fluid flow circuit via a single fluid access device.

Aspect 14. The method of any one of Aspects 11-12, wherein said fluid is drawn into the fluid flow circuit via a first fluid access device and at least a portion of a separated fluid constituent is conveyed out of the fluid flow circuit via a second fluid access device.

Aspect 15. The method of any one of Aspects 11-14, wherein said concentration of the fluid component within the fluid is substantially constant.

Aspect 16. The method of any one of Aspects 11-14, wherein said target concentration of the fluid component in said one of said first and second constituents is substantially constant.

Aspect 17. The method of any one of Aspects 11-14, wherein said concentration of the fluid component within the fluid and said target concentration of the fluid component in said one of said first and second constituents are substantially constant.

Aspect 18. The method of any one of Aspects 11-17, wherein said fluid is conveyed into the centrifuge chamber at said first and second rates during a single stage of a multi-stage separation procedure.

Aspect 19. The method of Aspect 18, further comprising determining a first radial position of an interface between separated fluid constituents within the centrifuge chamber while said fluid is being conveyed into the centrifuge chamber at said first rate during said single stage of said multi-stage separation procedure, and determining a second radial position of said interface between separated fluid constituents within the centrifuge chamber while said fluid is being conveyed into the centrifuge chamber at said second rate during said single stage of said multi-stage separation procedure, wherein the first radial position is based at least in part on the first rotation rate and on a first signal transmitted by an interface monitoring assembly while said fluid is being conveyed into the centrifuge chamber at said first rate, and the second radial position is based at least in part on the second rotation rate and on a second signal transmitted by an interface monitoring assembly while said fluid is being conveyed into the centrifuge chamber at said second rate.

Aspect 20. The method of any one of Aspects 11-19, wherein the first rate is greater than the second rate and the first rotation rate is greater than the second rotation rate.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A fluid processing device, comprising:

a controller programmed to execute a separation procedure;

a centrifuge configured to receive and rotate a continuous-flow centrifuge chamber of a fluid flow circuit so as to separate a fluid in the centrifuge chamber into at least first and second constituents during the separation procedure; and a pump system configured to convey said fluid through the fluid flow circuit and into the centrifuge chamber at first and second rates during the separation procedure, wherein the controller is configured to control the centrifuge to rotate the centrifuge chamber at a first rotation rate when the pump system is conveying said fluid into the centrifuge chamber at the first rate during the separation procedure, the controller is configured to determine that the pump system is conveying said fluid into the centrifuge chamber at the second rate during the separation procedure instead of at the first rate and to control the centrifuge to rotate the centrifuge chamber at a second rotation rate after determining that the pump system is conveying said fluid into the centrifuge chamber at the second rate during the separation procedure, and said first and second rotation rates are different, with each of the first and second rotation rates being based at least in part on a concentration of a fluid component within the fluid, the rate at which the pump system is conveying said fluid into the centrifuge chamber, and a target concentration of the fluid component in one of said first and second constituents and being controlled so as to achieve a substantially uniform separation efficiency.

2. The fluid processing device of claim 1, wherein said fluid comprises whole blood, one of said first and second constituents comprises packed red blood cells, said fluid component comprises red blood cells, and said target concentration of the fluid component in said one of said first and second constituents comprises a target hematocrit of the packed red blood cells.

3. The fluid processing device of claim 1, wherein the controller is configured to control the pump system to draw said fluid into the fluid flow circuit and to convey at least a portion of a separated fluid constituent out of the fluid flow circuit via a single fluid access device.

4. The fluid processing device of claim 1, wherein the controller is configured to control the pump system to draw said fluid into the fluid flow circuit via a first fluid access device and to convey at least a portion of a separated fluid constituent out of the fluid flow circuit via a second fluid access device.

5. The fluid processing device of claim 1, wherein said concentration of the fluid component within the fluid is substantially constant.

6. The fluid processing device of claim 1, wherein said target concentration of the fluid component in said one of said first and second constituents is substantially constant.

7. The fluid processing device of claim 1, wherein said concentration of the fluid component within the fluid and said target concentration of the fluid component in said one of said first and second constituents are substantially constant.

8. The fluid processing device of claim 1, wherein the controller is configured to control the pump system to convey said fluid through the fluid flow circuit and into the centrifuge chamber at said first and second rates during a single stage of a multi-stage separation procedure.

9. The fluid processing device of claim 8, further comprising an interface monitoring assembly configured to transmit a first signal to the controller indicative of a first radial position of an interface between separated fluid constituents within the centrifuge chamber while said fluid is being conveyed into the centrifuge chamber at the first rate during said single stage of said multi-stage separation procedure and to transmit a second signal to the controller indicative of a second radial position of the interface between separated fluid constituents within the centrifuge chamber while said fluid is being conveyed into the centrifuge chamber at the second rate during said single stage of said multi-stage separation procedure, wherein the controller is configured to determine the first radial position of said interface based at least in part on the first signal and on the first rotation rate and to determine the second radial position of said interface based at least in part on the second signal and on the second rotation rate.

10. The fluid processing device of claim 1, wherein the first rate is greater than the second rate and the first rotation rate is greater than the second rotation rate.

11. A method of separating a fluid, comprising:

conveying a fluid into a continuous-flow centrifuge chamber of a fluid flow circuit at first and second rates during a separation procedure;

determining that the fluid is being conveyed into the centrifuge chamber at the second rate during the separation procedure instead of at the first rate; and rotating the centrifuge chamber with a centrifuge so as to separate the fluid in the centrifuge chamber into at least first and second constituents, with the centrifuge rotating the centrifuge chamber at a first rotation rate when the fluid is being conveyed into the centrifuge chamber at the first rate during the separation procedure and at a second rotation rate after it has been determined that the fluid is being conveyed into the centrifuge chamber at the second rate during the separation procedure, wherein said first and second rotation rates are different, with each of the first and second rotation rates being based at least in part on a concentration of a fluid component within the fluid, the rate at which the fluid is being conveyed into the centrifuge chamber, and a target concentration of the fluid component in one of said first and second constituents and being controlled so as to achieve a substantially uniform separation efficiency.

12. The method of claim 11, wherein said fluid comprises whole blood, one of said first and second constituents comprises packed red blood cells, said fluid component comprises red blood cells, and said target concentration of the fluid component in said one of said first and second constituents comprises a target hematocrit of the packed red blood cells.

13. The method of claim 11, wherein said fluid is drawn into the fluid flow circuit and at least a portion of a separated fluid constituent is conveyed out of the fluid flow circuit via a single fluid access device.

14. The method of claim 11, wherein said fluid is drawn into the fluid flow circuit via a first fluid access device and at least a portion of a separated fluid constituent is conveyed out of the fluid flow circuit via a second fluid access device.

15. The method of claim 11, wherein said concentration of the fluid component within the fluid is substantially constant.

16. The method of claim 11, wherein said target concentration of the fluid component in said one of said first and second constituents is substantially constant.

17. The method of claim 11, wherein said concentration of the fluid component within the fluid and said target concentration of the fluid component in said one of said first and second constituents are substantially constant.

18. The method of claim 11, wherein said fluid is conveyed into the centrifuge chamber at said first and second rates during a single stage of a multi-stage separation procedure.

19. The method of claim 18, further comprising determining a first radial position of an interface between separated fluid constituents within the centrifuge chamber while said fluid is being conveyed into the centrifuge chamber at said first rate during said single stage of said multi-stage separation procedure, and determining a second radial position of said interface between separated fluid constituents within the centrifuge chamber while said fluid is being conveyed into the centrifuge chamber at said second rate during said single stage of said multi-stage separation procedure, wherein the first radial position is based at least in part on the first rotation rate and on a first signal transmitted by an interface monitoring assembly while said fluid is being conveyed into the centrifuge chamber at said first rate, and the second radial position is based at least in part on the second rotation rate and on a second signal transmitted by the interface monitoring assembly while said fluid is being conveyed into the centrifuge chamber at said second rate.

20. The method of claim 11, wherein the first rate is greater than the second rate and the first rotation rate is greater than the second rotation rate.

* * * * *